United States Patent
Izumori et al.

(10) Patent No.: US 9,932,617 B2
(45) Date of Patent: *Apr. 3, 2018

(54) KETOSE 3-EPIMERASE PRODUCED BY ARTHROBACTER GLOBIFORMIS

(71) Applicants: MATSUTANI CHEMICAL INDUSTRY CO., LTD., Itami-shi, Hyogo (JP); IZUMORING CO., LTD., Kita-gun, Kagawa (JP)

(72) Inventors: Ken Izumori, Kita-gun (JP); Pushpa Kiran Gullapalli, Itami (JP); Tomoya Shintani, Itami (JP); Ryo Kikkawa, Itami (JP)

(73) Assignee: MATSUTANI CHEMICAL INDUSTRY CO., LTD., Itami-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/759,620

(22) PCT Filed: Dec. 26, 2013

(86) PCT No.: PCT/JP2013/084978
§ 371 (c)(1),
(2) Date: Jul. 7, 2015

(87) PCT Pub. No.: WO2014/109254
PCT Pub. Date: Jul. 17, 2014

(65) Prior Publication Data
US 2015/0344925 A1    Dec. 3, 2015

(30) Foreign Application Priority Data

Jan. 8, 2013 (JP) ................................ 2013-001035

(51) Int. Cl.

| | |
|---|---|
| *C12N 9/90* | (2006.01) |
| *C12P 19/02* | (2006.01) |
| *C12P 19/24* | (2006.01) |
| *C12N 1/21* | (2006.01) |
| *C12N 15/61* | (2006.01) |
| *C12N 11/00* | (2006.01) |

(52) U.S. Cl.
CPC ............... *C12P 19/24* (2013.01); *C12N 9/90* (2013.01); *C12N 11/00* (2013.01); *C12P 19/02* (2013.01); *C12Y 503/01* (2013.01)

(58) Field of Classification Search
None
See application file for complete search history.

(56) References Cited

U.S. PATENT DOCUMENTS

| 5,411,880 A | 5/1995 | Izumori et al. |
|---|---|---|
| 2006/0041961 A1 | 2/2006 | Abad et al. |

| 2010/0129865 A1 | 5/2010 | Maruta et al. |
|---|---|---|
| 2010/0190225 A1 | 7/2010 | Oh et al. |
| 2014/0186925 A1 | 7/2014 | Izumori et al. |

FOREIGN PATENT DOCUMENTS

| EP | 1 586 652 A1 | 10/2005 |
|---|---|---|
| JP | 6-125776 A | 5/1994 |
| JP | 2001-011090 A | 1/2001 |
| JP | 2005-213227 A | 8/2005 |
| JP | 2008-541753 A | 11/2008 |
| WO | 2007/058086 A1 | 5/2007 |
| WO | 2013/005800 A1 | 1/2013 |

OTHER PUBLICATIONS

Morris, Studies on the metabolism of Arthrobacter globiformis, J. Gen. Microbiol., 1960, 11, 564-82.*
International Search Report dated Mar. 25, 2014, issued in corresponding application No. PCT/JP2013/084978 (4 pages).
Uechi, et al., "Gene Cloning and Characterization of L-Ribulose 3-epimerase from Mesorhizobium loti and Its Application to Rare Sugar Production", Biosci. Biotechnol. Biochem., Mar. 2013, vol. 77, No. 3, pp. 511-515, cited in ISR.
Zwick, et al., "Genomic Characterization of the *Bacillus cereus sensu lato* species: Backdrop to the evolution of *Bacillus anthracis*", *Bacillus cerus* comparative genomics, Genome Research, 2012, vol. 22, No. 8, pp. 1512-1524, cited in ISR.
NAD-dependent epimerase/dehydratase [Bacillus cereus MM3], GenBank, Accesin No. EEK67073, <http:www.ncbi.nlm.nih.gov/protein/EEK67073>, Apr. 30, 2009, cited in ISR (40 pages).
Matsuo, et al., "Dietary D-psicose, a C-3 epimer of D-fructose, suppresses the activity of hepatic lipogenic enzymes in rats", Asia Pacific Journal of Clinical Nutrition, 2001, vol. 10, No. 3, pp. 233-237.
Matsuo, et. al., "D-Psicose, a rare sugar that provides no energy and additionally beneficial effects for clinical nutrition" Asia Pacific Journal of Clinical Nutrition, 2004, vol. 13 (Suppl), pp. S127.
Izumori, et al., "A New Enzyme, D-Ketohexose 3-Epimerase, from *Pseudomonas* sp. ST-24", Biosci. Biotech. Biochem, 1993, vol. 57, No. 6, pp. 1037-1039.

* cited by examiner

*Primary Examiner* — Robert B Mondesi
*Assistant Examiner* — Todd M Epstein
(74) *Attorney, Agent, or Firm* — Westerman, Hattori, Daniels & Adrian, LLP

(57) ABSTRACT

There are provided a highly safe epimerase usable in food industry, and a method for producing a ketose. The epimerase is a ketose 3-epimerase obtainable from a microorganism of the genus *Arthrobacter*, and having the amino acid sequence represented by SEQ ID NO: 1 of the Sequence Listing, and (1) substrate specificity whereby a D- or L-ketose is epimerized at position 3 to produce a corresponding D- or L-ketose, and (2) the highest substrate specificity for D-fructose and D-psicose among D- and L-ketoses. The ketose 3-epimerase is also represented by SEQ ID NO: 3 or SEQ ID NO: 4 of the Sequence Listing, and epimerizes a D- or L-ketose at position 3 to produce a corresponding D- or L-ketose.

8 Claims, 12 Drawing Sheets

[fig.1]
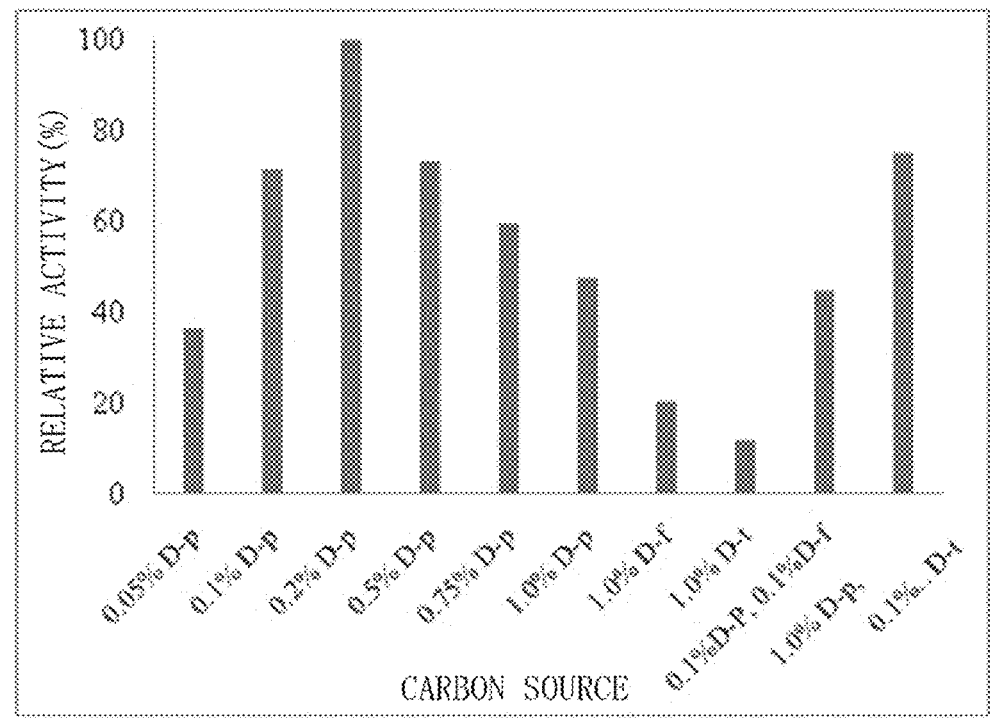
[fig.2]
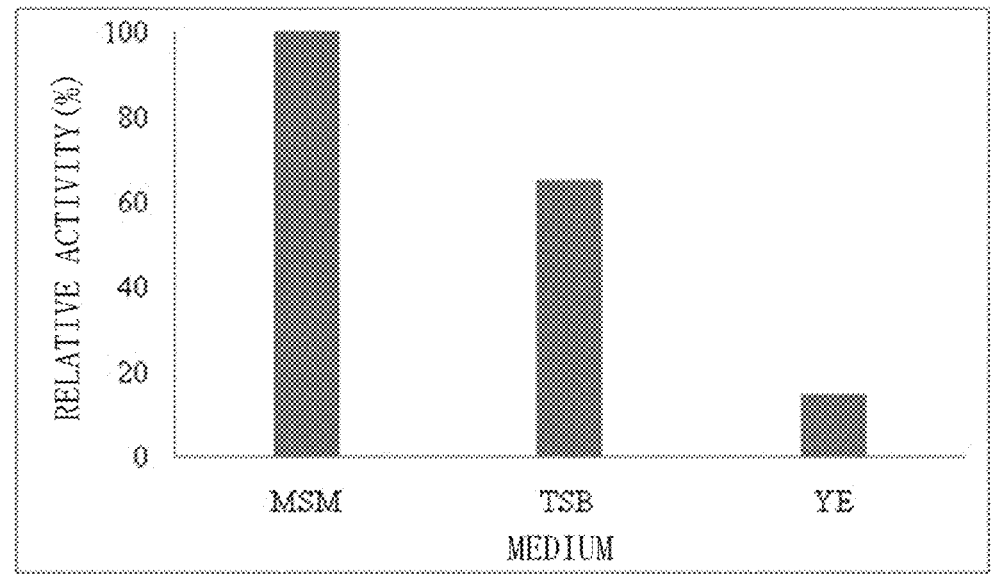

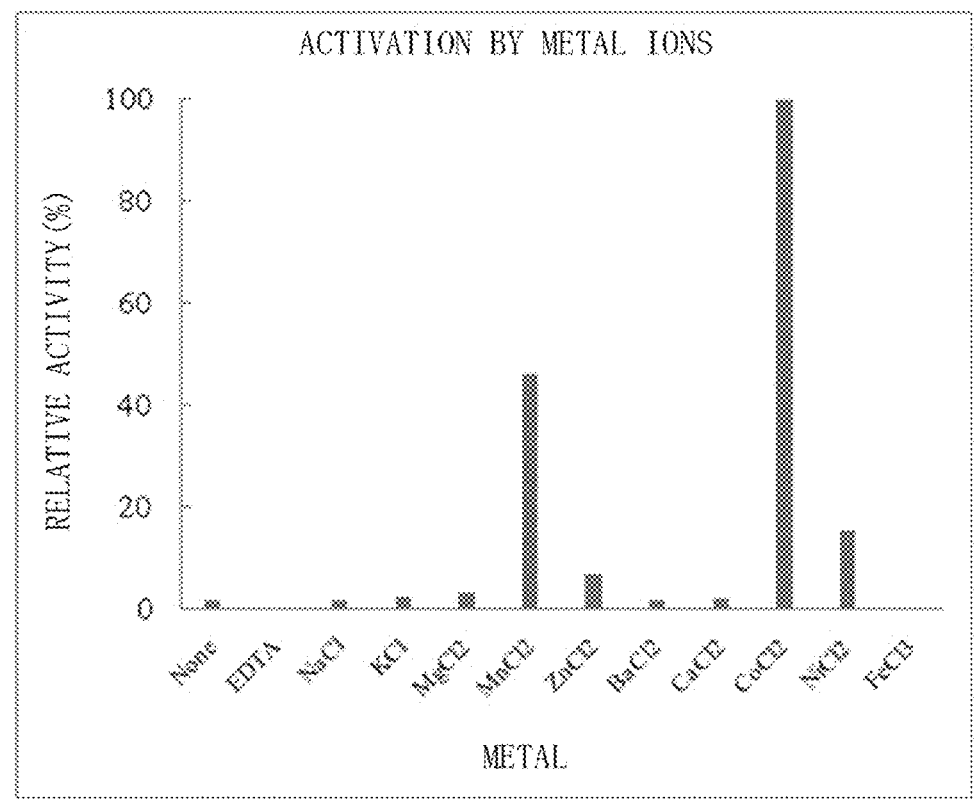

[fig.4]
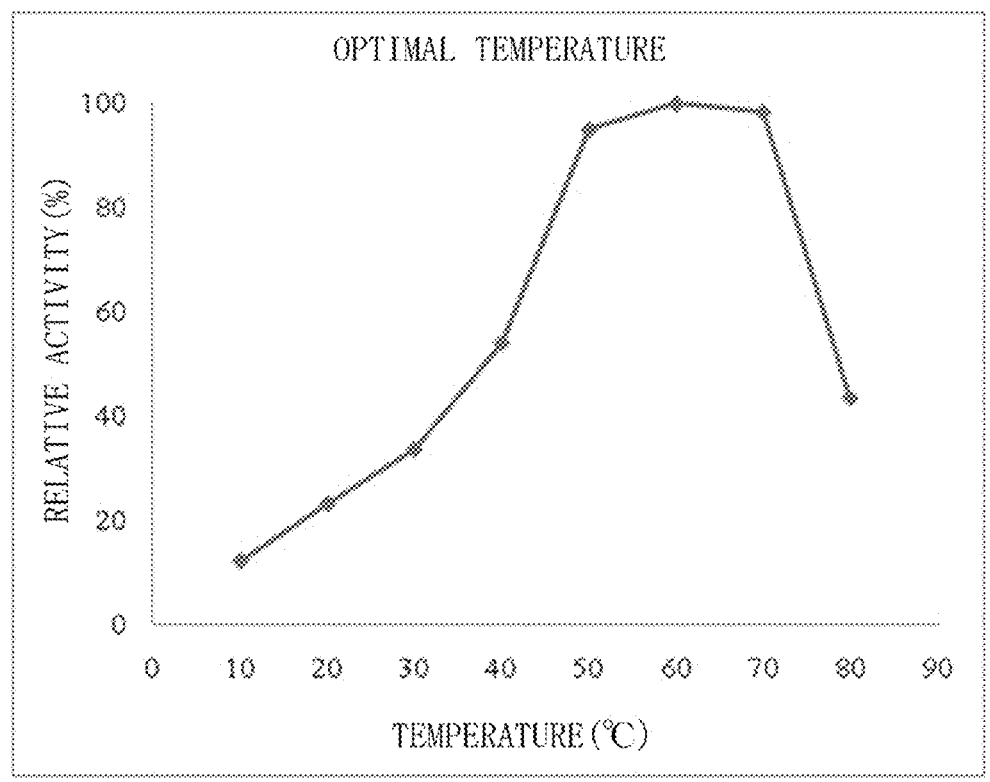

[fig.5]
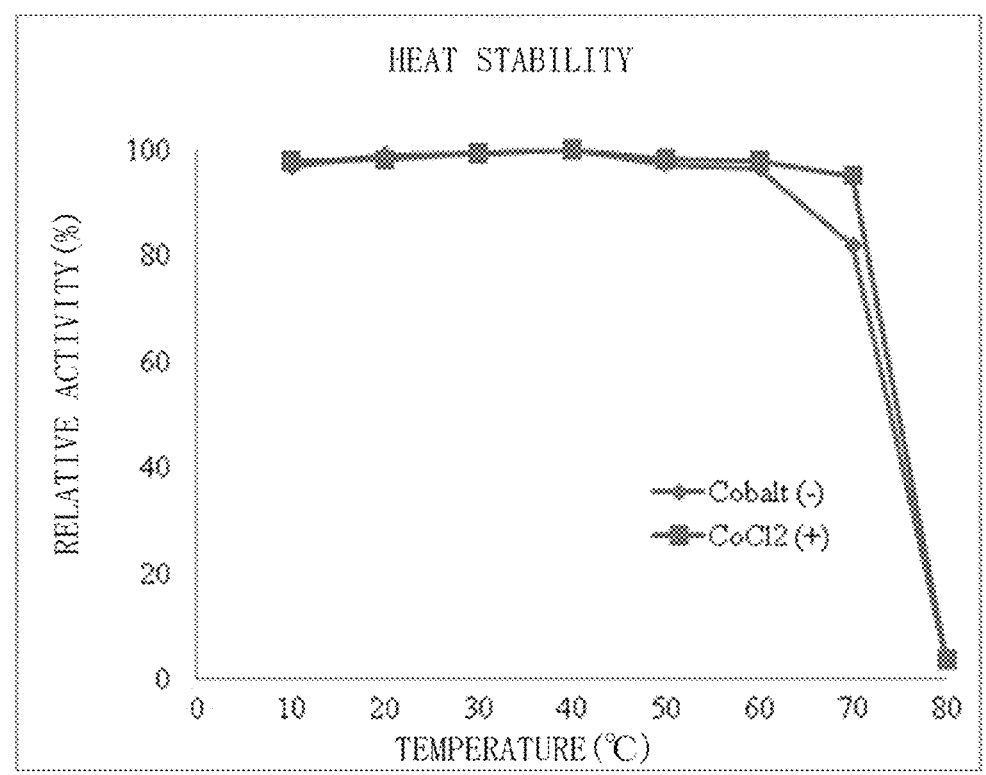

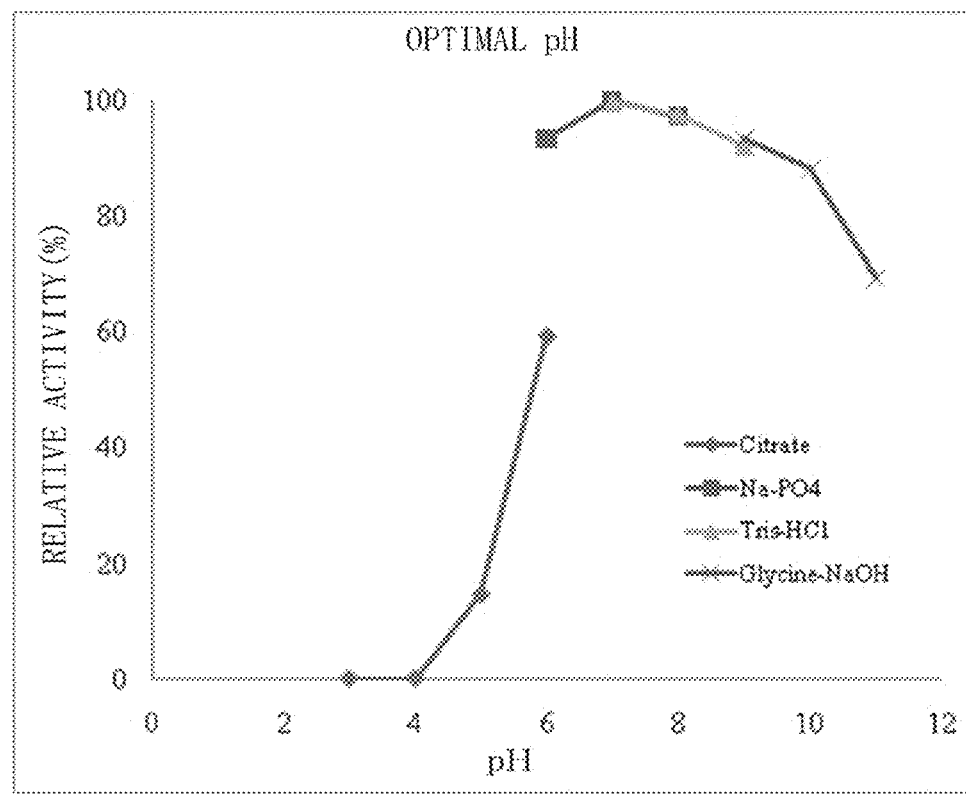
[fig.6]

[fig.7]
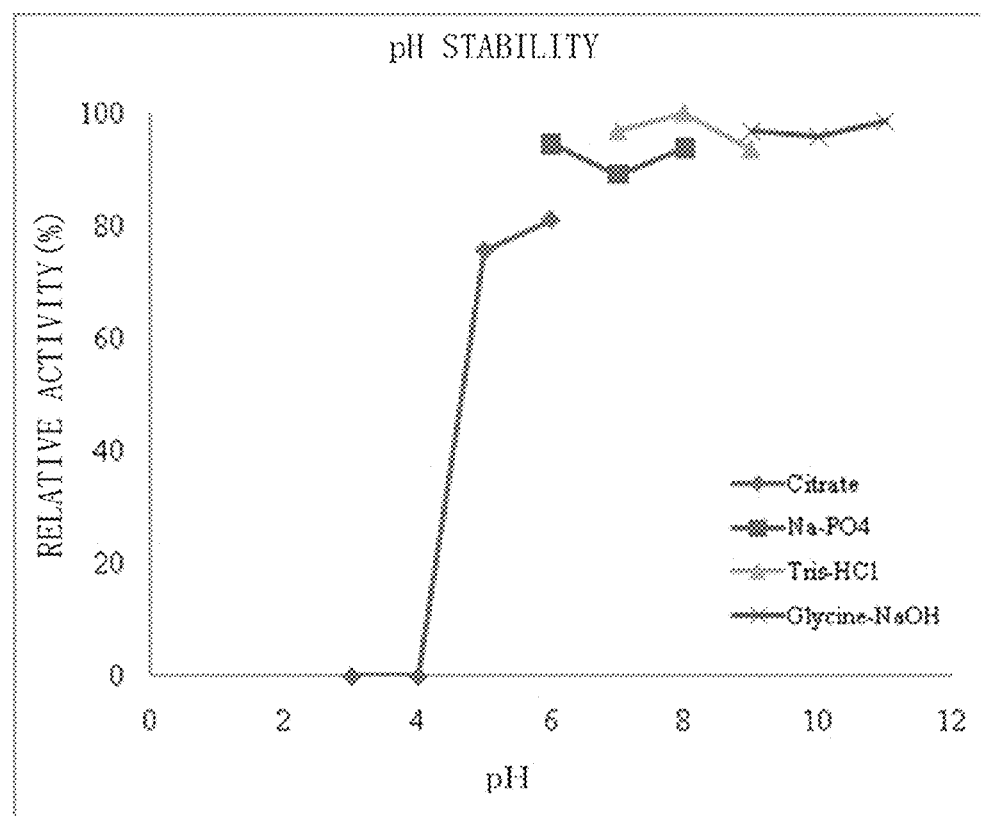

[fig.8]
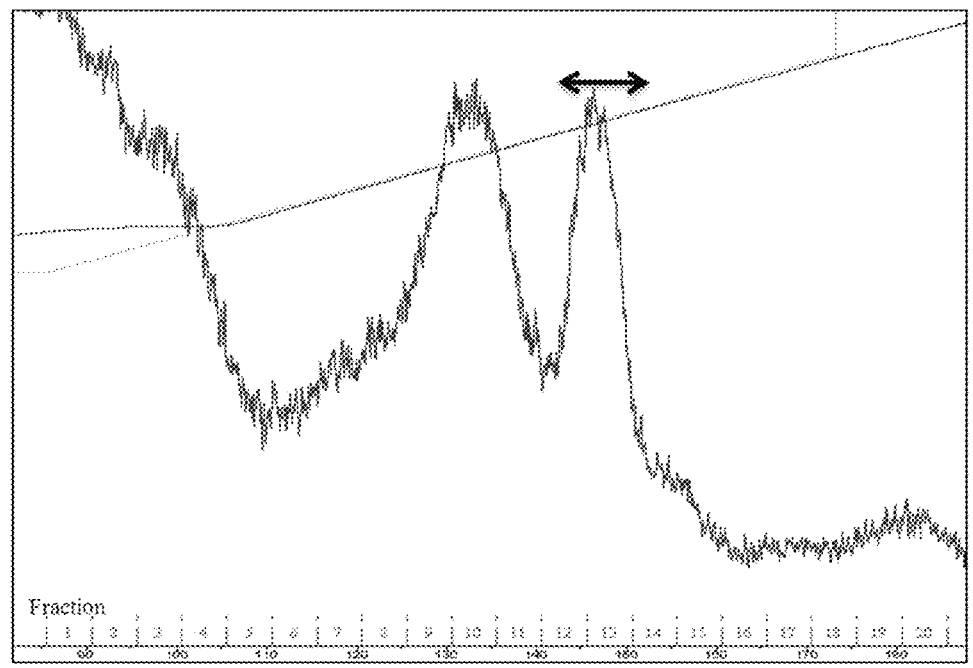
[fig.9]
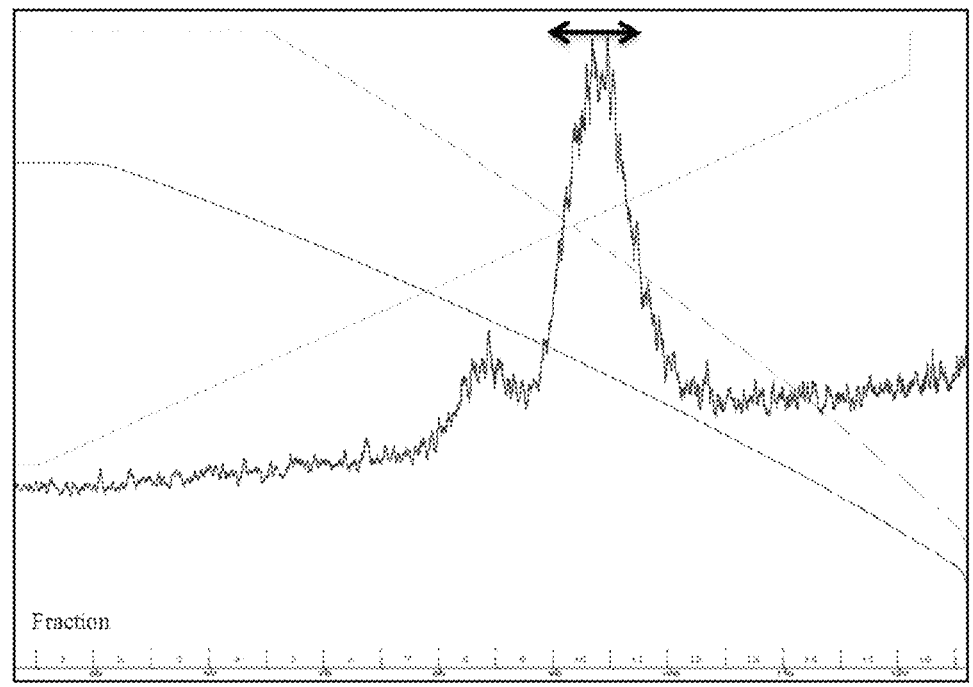

[fig.10]
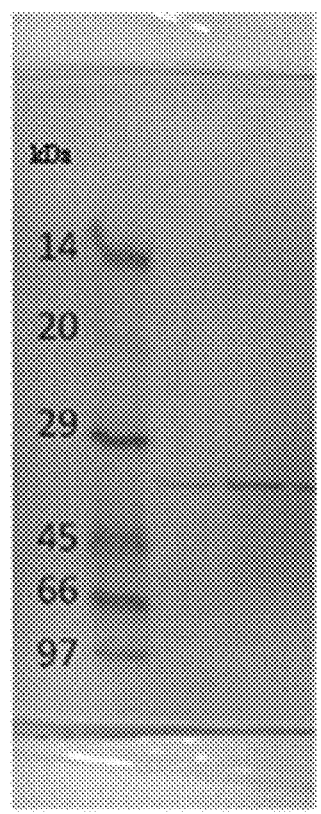
[fig.11]
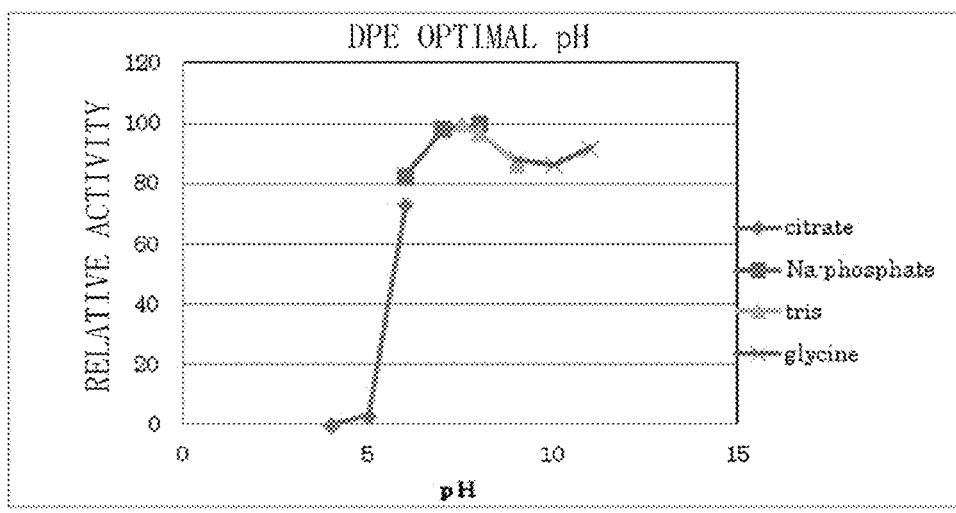

[fig.12]
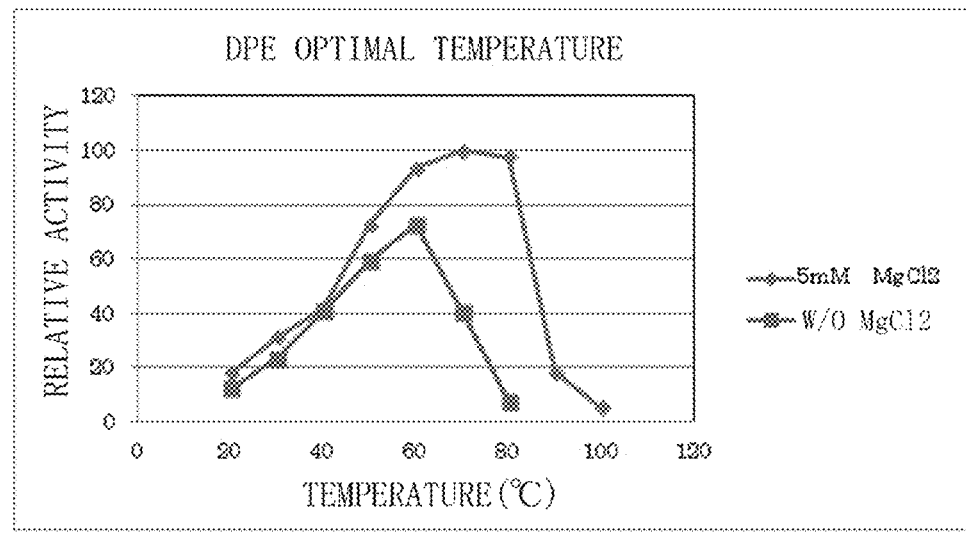
[fig.13]
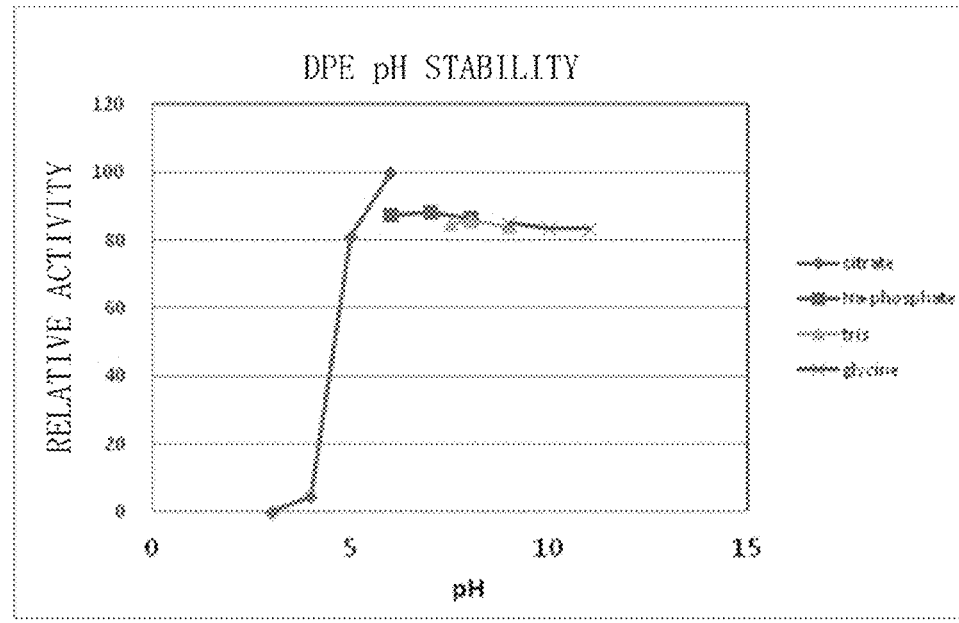

[fig.14]
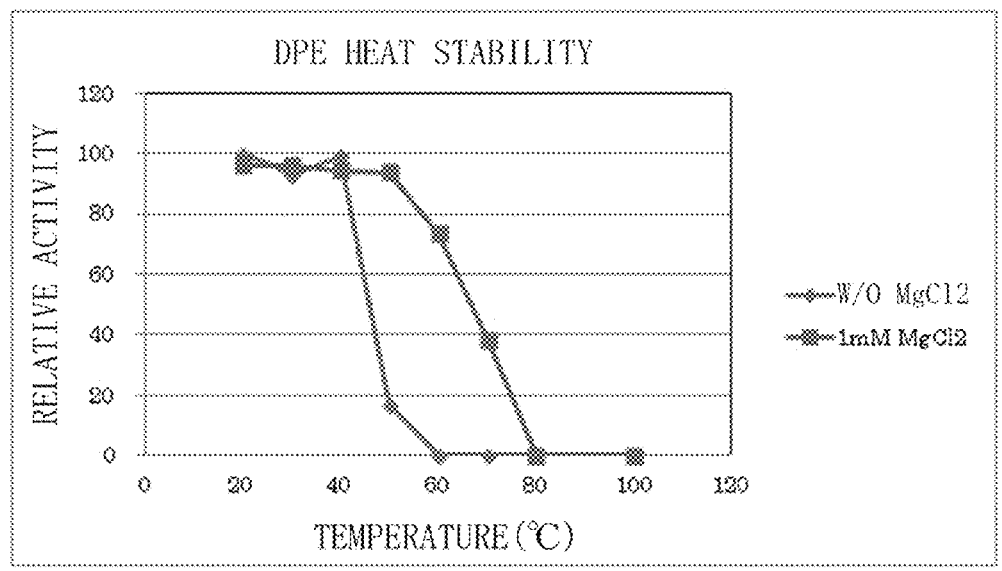

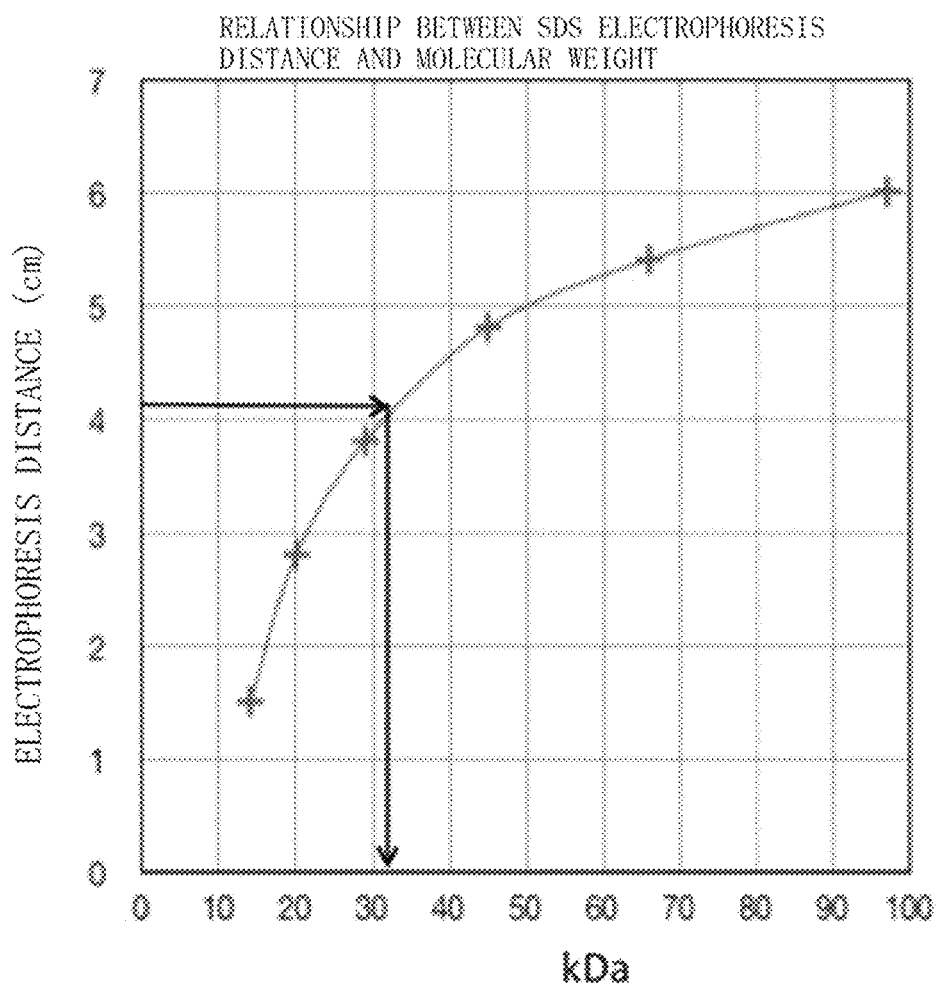
[fig.15]

[fig.16]
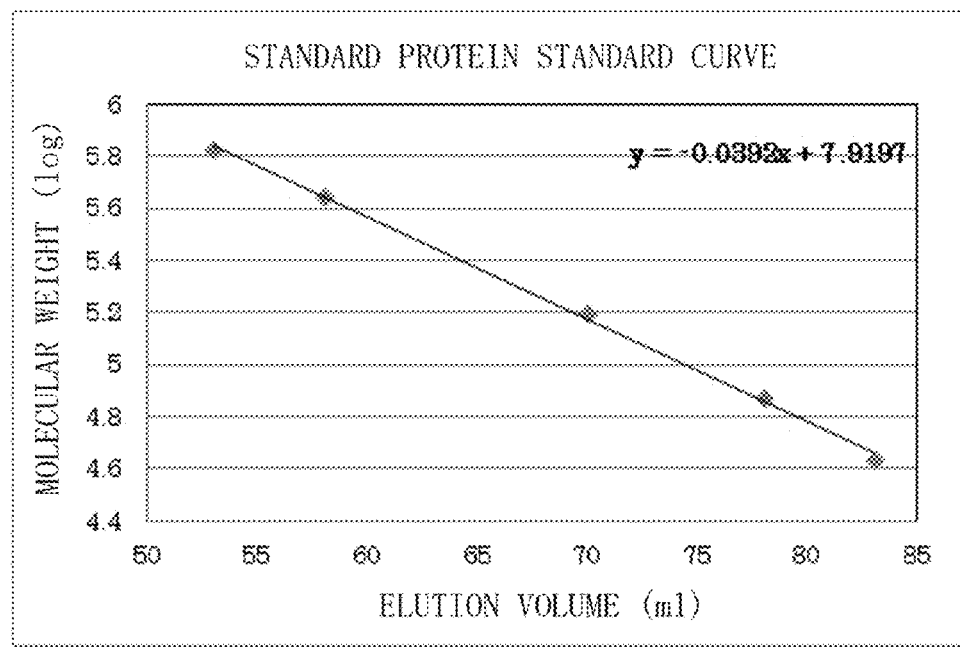
[fig.17]
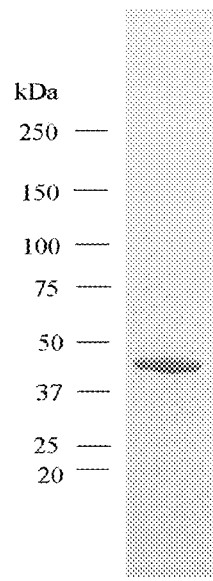

SEQUENCE LISTING

```
<160> NUMBER OF SEQ ID NOS: 4

<210> SEQ ID NO 1
<211> LENGTH: 289
<212> TYPE: PRT
<213> ORGANISM: Arthrobacter globiformis

<400> SEQUENCE: 1

Met Lys Ile Gly Cys His Gly Leu Val Trp Thr Gly His Phe Asp Ala
1               5                   10                  15

Glu Gly Ile Arg Tyr Ser Val Gln Lys Thr Arg Glu Ala Gly Phe Asp
                20                  25                  30

Leu Val Glu Phe Pro Leu Met Asp Pro Phe Ser Phe Asp Val Gln Thr
            35                  40                  45

Ala Lys Ser Ala Leu Ala Glu His Gly Leu Ala Ala Ser Ala Ser Leu
        50                  55                  60

Gly Leu Ser Asp Ala Thr Asp Val Ser Ser Glu Asp Pro Ala Val Val
65                  70                  75                  80

Lys Ala Gly Glu Glu Leu Leu Asn Arg Ala Val Asp Val Leu Ala Glu
                85                  90                  95

Leu Gly Ala Thr Asp Phe Cys Gly Val Ile Tyr Ser Ala Met Lys Lys
            100                 105                 110

Tyr Met Glu Pro Ala Thr Ala Ala Gly Leu Ala Asn Ser Lys Ala Ala
        115                 120                 125

Val Gly Arg Val Ala Asp Arg Ala Ser Asp Leu Gly Ile Asn Val Ser
    130                 135                 140

Leu Glu Val Val Asn Arg Tyr Glu Thr Asn Val Leu Asn Thr Gly Arg
145                 150                 155                 160

Gln Ala Leu Ala Tyr Leu Glu Glu Leu Asn Arg Pro Asn Leu Gly Ile
                165                 170                 175

His Leu Asp Thr Tyr His Met Asn Ile Glu Glu Ser Asp Met Phe Ser
            180                 185                 190

Pro Ile Leu Asp Thr Ala Glu Ala Leu Arg Tyr Val His Ile Gly Glu
        195                 200                 205

Ser His Arg Gly Tyr Leu Gly Thr Gly Ser Val Asp Phe Asp Thr Phe
    210                 215                 220

Phe Lys Ala Leu Gly Arg Ile Gly Tyr Asp Gly Pro Val Val Phe Glu
225                 230                 235                 240

Ser Phe Ser Ser Ser Val Val Ala Pro Asp Leu Ser Arg Met Leu Gly
```

245                 250                 255
Ile Trp Arg Asn Leu Trp Ala Asp Asn Glu Glu Leu Gly Ala His Ala
            260                 265                 270

Asn Ala Phe Ile Arg Asp Lys Leu Thr Ala Ile Lys Thr Ile Glu Leu
       275                 280                 285

His

<210> SEQ ID NO 2
<211> LENGTH: 870
<212> TYPE: DNA
<213> ORGANISM: Arthrobacter globiformis

<400> SEQUENCE: 2

| | |
|---|---:|
| atgaaaattg gttgccatgg cctggtttgg accggccact tcgacgctga aggcattcgc | 60 |
| tactccgtcc agaaaaccag ggaagccggt ttcgacctcg ttgagttccc gctcatggat | 120 |
| ccgttctcct tcgatgtgca gacggccaag tccgcactgg ccgaacatgg gctggcggcc | 180 |
| tcggcatctc tgggactctc ggacgccact gacgtaagca gcgaagatcc cgccgtcgtg | 240 |
| aaggcagggg aggagctgct caaccgcgcc gtggatgttc tggccgaact gggtgcgacg | 300 |
| gatttctgcg gcgtgattta tagcgccatg aagaagtaca tggagccggc aactgctgcc | 360 |
| gggctggcca acagcaaggc agccgtcggg cgggtcgcgg accgggcatc ggatctgggg | 420 |
| atcaatgttt cgctggaggt cgtcaacagg tacgaaacca acgtactgaa caccggacgt | 480 |
| caggcccttg cctacttgga ggagctcaac cggccgaacc tgggcatcca cctggacact | 540 |
| taccacatga acattgagga atcggacatg ttctccccga tcctggacac cgcggaggcc | 600 |
| ctgcggtacg tccatatcgg cgaaagccac cgcggctacc tcggcacggg aagcgttgac | 660 |
| ttcgacactt tcttcaaggc cctcggccgc atcggctatg acggaccggt tgtcttcgaa | 720 |
| tcgttctcct cctccgtcgt ggcaccggat ctgagccgga tgctcggcat ctggcgcaac | 780 |
| ctgtgggccg acaacgagga actgggtgcg cacgcgaatg ccttcatccg cgacaagctc | 840 |
| accgcgatca agaccatcga actgcactaa | 870 |

<210> SEQ ID NO 3
<211> LENGTH: 870
<212> TYPE: DNA
<213> ORGANISM: Arthrobacter globiformis

<400> SEQUENCE: 3

| | |
|---|---:|
| atgaaaattg gttgtcatgg cctggtttgg accggccact tcgacgctga aggcattcgc | 60 |
| tactccgtcc agaaaaccag ggaagccggt ttcgacctcg ttgagttccc gctcatggat | 120 |
| ccgttctcct tcgatgtgca gacggccaag tccgcactgg ccgaacatgg gctggcggcc | 180 |
| tcggcatctc tgggactctc ggacgccact gacgtaagca gcgaagatcc cgccgtcgtg | 240 |
| aaggcagggg aggagctgct caaccgcgcc gtggatgttc tggccgaact gggtgcgacg | 300 |
| gatttctgcg gcgtgattta tagcgccatg aagaagtaca tggagccggc aactgctgcc | 360 |
| gggctggcca acagcaaggc agccgtcggg cgggtcgcgg accgggcatc ggatctgggg | 420 |
| atcaatgttt cgctggaggt cgtcaacagg tacgaaacca acgtactgaa caccggacgt | 480 |
| caggcccttg cctacttgga ggagctcaac cggccgaacc tgggcatcca cctggacact | 540 |
| taccacatga acattgagga atcggacatg ttctccccga tcctggacac cgcggaggcc | 600 |
| ctgcggtacg tccatatcgg cgaaagccac cgcggctacc tcggcacggg aagcgttgac | 660 |
| ttcgacactt tcttcaaggc cctcggccgc atcggctatg acggaccggt tgtcttcgaa | 720 |

```
tcgttctcct cctccgtcgt ggcaccggat ctgagccgga tgctcggcat ctggcgcaac      780
ctgtgggccg acaacgagga actgggtgcg cacgcgaatg ccttcatccg cgacaagctc      840
accgcgatca agaccatcga actgcactaa                                        870
```

<210> SEQ ID NO 4
<211> LENGTH: 341
<212> TYPE: PRT
<213> ORGANISM: Arthrobacter globiformis

<400> SEQUENCE: 4

```
Met Lys Ile Leu Ile Leu Gly Gly Thr Arg Phe Leu Gly Arg Ala Phe
1               5                   10                  15

Val Glu Glu Ala Leu Gln Arg Gly His Glu Val Thr Leu Phe Asn Arg
                20                  25                  30

Gly Thr Asn Lys Glu Ile Phe Pro Glu Val Glu Gln Leu Ile Gly Asp
            35                  40                  45

Arg Asn Gly Asp Val Ser Ser Leu Glu Asn Arg Lys Trp Asp Val Val
        50                  55                  60

Ile Asp Thr Cys Gly Phe Ser Pro His His Ile Arg Asn Val Gly Glu
65                  70                  75                  80

Val Leu Lys Asp Asn Ile Glu His Tyr Ile Phe Ile Ser Ser Leu Ser
                85                  90                  95

Val Tyr Lys Asp Trp Ile Pro His His Ile Lys Glu Asp Tyr Ile Leu
            100                 105                 110

Gln Pro Glu Pro Thr Gly Asp Gln Ile Lys Ala Val Glu Asn Gly Glu
        115                 120                 125

Ile Ser Pro Tyr Glu His Tyr Gly Ala Leu Lys Val Leu Cys Glu Lys
130                 135                 140

Glu Ala Glu Lys Tyr Trp Pro Gly Arg Val Leu His Val Arg Ala Gly
145                 150                 155                 160

Leu Leu Ser Gly Met Phe Asp Tyr Thr Asp Arg Leu Pro Tyr Trp Ile
                165                 170                 175

Gly Arg Val Ala Lys Gly Gly Lys Val Leu Val Pro Gly Arg Lys Asn
            180                 185                 190

Arg Pro Val Gln Ile Val Asp Ile Lys Asp Val Ala Asn Trp Gly Leu
        195                 200                 205

Asn Met Ala Glu Asn Asn Lys Ala Gly Ile Phe Asn Val Thr Gly Pro
210                 215                 220

Asn Tyr Glu Leu Thr Met Ala Gly Leu Leu Asn Thr Cys Lys Lys Val
225                 230                 235                 240

Thr Asn Ser Asp Ala Glu Phe Val Trp Val Glu Glu Ser Phe Met Asn
                245                 250                 255

Glu His Lys Val Gln Pro Trp Thr Glu Met Pro Leu Trp Leu Pro Glu
            260                 265                 270

Thr Ile Ser Leu Glu Gly Glu Thr Lys Pro Trp Lys Gly Gly Phe Ser
        275                 280                 285

Ile Ser Ile Glu Ser Ala Val Lys Glu Gly Leu Thr Phe Arg Arg Leu
290                 295                 300

Glu Glu Thr Val Thr Asp Val Tyr Ala Trp Met Lys Ser Val Asp Glu
305                 310                 315                 320

Trp Glu Leu Lys Ala Gly Ile Ser Gly Glu Arg Glu Lys Arg Leu Leu
                325                 330                 335

Glu Asn Trp Tyr Gln
            340
```

KETOSE 3-EPIMERASE PRODUCED BY ARTHROBACTER GLOBIFORMIS

TECHNICAL FIELD

The present invention relates to a ketose 3-epimerase having a specific amino acid sequence, and to a method for producing ketose with the use of the enzyme. Specifically, the invention relates to a ketose 3-epimerase obtainable from *Arthrobacter globiformis* M30 (accession number NITE BP-1111), and having a specific amino acid sequence, and (A) substrate specificity whereby a D- or L-ketose is epimerized at position 3 to produce a corresponding D- or L-ketose, and (B) the highest substrate specificity for D-fructose and D-psicose among D- and L-ketoses. The present invention also relates to a method for producing ketose with the enzyme.

BACKGROUND ART

D-psicose, an epimer of D-fructose, is very similar to D-fructose in terms of the intensity and the variety of sweetness. However, unlike D-fructose, D-psicose is hardly metabolized upon being absorbed in the body, and has a low caloric contribution. PTL 1 describes advantageously using D-psicose as a low calorie sweetener for production of low calorie food and drinks. That is, D-psicose has potential use as an active ingredient of diet food. Sugar alcohols, widely used as non-sugar sweeteners, cause side effects such as diarrhea when ingested above the specified amounts. D-psicose has fewer such side effects. Further, because D-psicose is hardly metabolized in human body, the caloric value is nearly zero, and suppresses the lipid synthetase activity and lowers abdominal fat. This makes D-psicose also useful as a sweetener beneficial to body weight reduction (see, for example, NPL 1 and NPL 2). PTL 2 describes that potentially advantageous use of D-psicose can be advantageously used for products such as food with health claims, food and drinks for diabetes patients, and slimming food and drinks because D-psicose has the blood sugar level suppressing effect. From these viewpoints, D-psicose has attracted a great deal of interest as a food with health claims, and a diet sweetener, and there is a growing need for the development of an efficient and safe method of producing D-psicose in food industry.

NPL 3 discloses a D-ketose 3-epimerase derived from *Pseudomonas cichorii* ST-24, and using this enzyme for production of D-psicose from D-fructose. However, as the alternative name D-tagatose 3-epimerase suggests, the enzyme has the highest specificity for D-tagatose, and its activity on D-fructose is known to be relatively weak. Further, the *Pseudomonas cichorii*, a phytopathogenic bacterium, has a very poor capability for producing D-ketose 3-epimerase, and is not suited for industrial use. There is accordingly a need for a microorganism different from *Pseudomonas*, and that has a high ketose 3-epimerase production capability for safe food production. A novel ketose 3-epimerase having high specificity for D-fructose, and suited for D-psicose production is also needed.

PTL 3 attempts to provide a novel ketose 3-epimerase, a method of production thereof, a DNA encoding the enzyme, a recombinant DNA and a transformant containing the DNA, and a method for producing ketose with the enzyme. This publication actually provides a ketose 3-epimerase that can be obtained from microorganisms of the genus *Rhizobium*, a method of production thereof, a DNA encoding the enzyme, a recombinant DNA and a transformant containing the DNA, and a method that uses the enzyme to epimerize a D- or L-ketose at position 3 and produce a corresponding D- or L-ketose. PTL 4 develops a method for producing D-psicose with a D-psicose epimerase (hereinafter, "psicose 3-epimerase") derived from *Agrobacterium tumefaciens*.

As described above, the foregoing problems are addressed by the studies of methods that enzymatically produce D-psicose by using D-fructose as a substrate. However, the methods developed to date are problematic in terms of the safety of D-psicose production for food.

CITATION LIST

Patent Literature

PTL 1: JP-A-2001-011090
PTL 2: JP-A-2005-213227
PTL 3: WO2007/058086
PTL 4: JP-T-2008-541753 (the term "JP-T" as used herein means a published Japanese translation of a PCT patent application)

Non-Patent Literature

NPL 1: Matsuo, T., Y. Baba, M. Hashiguchi, K. Takeshita, K. Izumori and H. Suzuki, Asia Pac. J. Clin. Nutr., 10: 233-237 (2001)
NPL 2: Matsuo, T. and K. Izumori, AsiaPac. J. Clin. Nutr., 13:S127 (2004)
NPL 3: Ken Izumori et al., Biosci. Biotech. Biochem., 57, 1037-1039 (1993)

SUMMARY OF INVENTION

Solution to Problem

Objects of the present invention are to obtain a novel ketose 3-epimerase that catalyzes the isomerization of D-fructose to D-psicose with high yield, which are derived from a bacterial strain of being considered to have essentially no toxicity and listed in the List of Existing Food Additives for food production, and to provide a method for producing ketose with the enzyme.

The present inventors collected soil from different places as the occasion permitted, and isolated microorganisms, except *Pseudomonas*, from the soil to search for a microorganism capable of producing a ketose 3-epimerase. The present inventors diligently continued the search for such microorganisms by focusing on bacterial strains considered to have essentially no toxicity, and that are approved for food applications in the equivalent lists published in Europe and the US, in addition to the List of Existing Food Additives issued in Japan.

The search isolated large numbers of bacterial strains, and found microorganisms of the genus *Arthrobacter* that produced a novel ketose 3-epimerase. The novel ketose 3-epimerase derived from such microorganisms was found to act on position 3 of a D- or L-ketose, and have a wide range of substrate specificity for the catalysis of the epimerization to a corresponding D- or L-ketose. It was found, rather surprisingly, that the substrate specificity was the highest for D-fructose and D-psicose among D- and L-ketoses, and the enzyme was suited for D-psicose production from D-fructose. The present invention was completed upon establishing a novel ketose 3-epimerase obtainable from microorganisms of the genus *Arthrobacter*, a method of production thereof, and a ketose conversion method and a ketose producing method using the enzyme.

Specifically, the present invention is intended to provide a ketose 3-epimerase obtainable from microorganisms of the genus *Arthrobacter*, and a method for epimerizing a D- or L-ketose at position 3, and producing a corresponding D- or L-ketose with the enzyme.

Microorganisms of the genus *Arthrobacter* have a relatively high capability for producing the novel ketose 3-epimerase, and, unlike *Pseudomonas cichorii*, are not pathogenic to plants. The ketose 3-epimerase of the present invention obtainable from such microorganisms is a good catalyst for the mutual conversion of D-psicose and D-fructose in particular, and is useful for D-psicose production from D-fructose.

Solution to Problem

The gist of the present invention lies in the ketose 3-epimerases set forth in the following (1) to (5).

(1) A ketose 3-epimerase of *Arthrobacter globiformis* M30 (accession number NITE BP-1111) origin comprising a partial amino acid sequence represented by the amino acid sequence of SEQ ID NO: 1 of the Sequence Listing, the ketose 3-epimerase having the following substrate specificities (A) and (B) with the physical and chemical properties set forth in (A) to (B) below, (A) substrate specificity whereby a D- or L-ketose is epimerized at position 3 to produce a corresponding D- or L-ketose, and (B) the highest substrate specificity for D-fructose and D-psicose among D- and L-ketoses.

(2) The ketose 3-epimerase according to (1), wherein the ketose 3-epimerase has the following physical and chemical properties (a) to (f):

(a) molecular weight:
a homotetramer structure having a subunit molecular weight of 32 kDa, with a subunit molecular weight of about 32 kDa as measured by SDS-PAGE, and a molecular weight of 120 kDa as measured by gel filtration;

(b) optimal pH:
6 to 11 under 30° C., 30-min reaction conditions in the presence of 20 mM magnesium ($Mg^{2+}$);

(c) optimal temperature:
60 to 80° C. under pH 7.5, 30-min reaction conditions in the presence of 20 mM magnesium ($Mg^{2+}$);

(d) pH stability:
stable in at least a pH range of 5 to 11 under 4° C., 24-hour maintained conditions;

(e) heat stability:
stable at about 50° C. or less under pH 7.5, 1-hour maintained conditions in the presence of 4 mM magnesium ions ($Mg^{2+}$), and stable at about 40° C. or less in the absence of magnesium ions ($Mg^{2+}$); and (f) metal ion activation:
activatable by divalent manganese ions ($Mn^{2+}$), divalent cobalt ions ($Co^{2+}$), and calcium ($Ca^{2+}$) and magnesium ions ($Mg^{2+}$).

(3) The ketose 3-epimerase according to (1) or (2), wherein the ketose 3-epimerase has the following substrate specificities 1 to 8:
1. 43.8% relative activity for a D-fructose substrate;
2. 100% activity for a D-psicose substrate;
3. 1.13% relative activity for a D-sorbose substrate;
4. 18.3% relative activity for a D-tagatose substrate;
5. 0.97% relative activity for an L-fructose substrate;
6. 21.2% relative activity for an L-psicose substrate;
7. 16.6% relative activity for an L-sorbose substrate; and
8. 44.0% relative activity for an L-tagatose substrate, the relative activity for each ketose being an activity relative to the epimerization activity for D-psicose which is taken as 100.

The gist of the present invention also lies in a ketose 3-epimerase encoded by a gene with the following specific base sequences.

(4) A ketose 3-epimerase that epimerizes position 3 of D- or L-ketose to produce a corresponding D- or L-ketose, the ketose 3-epimerase being encoded by the base sequence represented by SEQ ID NO: 3 or SEQ ID NO: 4 of the Sequence Listing, the base sequence represented by SEQ ID NO: 3 or SEQ ID NO: 4 of the Sequence Listing with the deletion, substitution, or addition of one or more bases that retains the activity of the encoded enzyme, or a complementary base sequence thereof.

(5) The ketose 3-epimerase according to (7), wherein the ketose 3-epimerase is D-psicose isomerase.

The gist of the present invention also lies in the ketose conversion method set forth in (6), and the ketose producing method set forth in (7).

(6) A ketose conversion method comprising causing the ketose 3-epimerase of any one of (1) to (5) to act on a solution containing one or more ketoses selected from D- and L-ketoses, and epimerize the one or more ketoses at position 3.

(7) A ketose producing method comprising causing the ketose 3-epimerase of any one of (1) to (5) to act on a solution containing one or more ketoses selected from D- and L-ketoses, and epimerize the one or more ketoses at position 3 to produce a corresponding ketose, and collecting the ketose.

Advantageous Effects of Invention

The present invention has the following advantageous effects.

1. The most notable feature of using the present enzyme derived from *Arthrobacter globiformis* in food industry is the safety of the bacteria.

2. The optimal pH of D-psicose producing bacteria is 7 to 9 for the genus *Pseudomonas*, 9 to 9.5 for the genus *Rhizobium*, and 7 to 8 for the genus *Agrobacterium*. On the other hand, the optimal pH range of the enzyme produced by the present bacterial strain is 6 to 8, and D-psicose production is possible also in a less coloring pH range of 7 or less.

3. There is a report based on 30-min enzyme activity measurement that activity increases in the presence of $Mn^{2+}$, $Mg^{2+}$ in the genus *Rhizobium*, and in the presence of $Co^{2+}$, $Mn^{2+}$ in the genus *Agrobacterium*. The present enzyme has been shown to increase activity in the presence of $Mn^{2+}$, or $Co^{2+}$. The activity also increases in the presence of $Mg^{2+}$, $Ca^{2+}$.

4. Reaction is possible in a wider temperature range compared to conventional enzymes.

5. Activity is high for the reaction from L-tagatose to L-sorbose.

6. Bacteria with activity are obtained even when the amount of the D-psicose added to a medium is as small as 0.15%.

7. Enzyme activity remains even with water, and reaction from fructose to psicose proceeds.

8. Growth rate is greater than that of *Pseudomonas cichorii*.

9. Ketose 3-epimerases with the base sequences represented by SEQ ID NO: 2 and SEQ ID NO: 3 of the Sequence Listing have an enzyme activity that is increased about 30 to 37 fold.

With the present invention, a novel ketose 3-epimerase that catalyzes the isomerization of D-fructose to D-psicose with high yield can be obtained from a bacterial strain approved in the List of Existing Food Additives for food production, and that is considered to have essentially no toxicity. The present invention also can provide a ketose producing method using the enzyme.

Specifically, the present invention can provide a ketose 3-epimerase obtainable from microorganisms of the genus *Arthrobacter*, and a method that uses the enzyme to epimerize a D- or L-ketose at position 3 and produce a corresponding D- or L-ketose. The ketose 3-epimerase of the present invention obtainable from such microorganisms is a good catalyst for the mutual conversion of D-psicose and D-fructose in particular, and is useful for D-psicose production from D-fructose.

BRIEF DESCRIPTION OF DRAWINGS

FIG. 1 is a diagram representing the effect of various carbon sources on enzyme yield with inorganic salt media.

FIG. 2 is a diagram representing the effect of various media on enzyme yield.

FIG. 3 is a diagram representing the effect of metal ions on D-PE activity.

FIG. 4 is a diagram representing optimal temperature.

FIG. 5 is a diagram representing heat stability.

FIG. 6 is a diagram representing optimal pH.

FIG. 7 is a diagram representing pH stability.

FIG. 8 is a diagram representing separation and elution by ion exchange chromatography.

FIG. 9 is diagram representing separation and elution by hydrophobic chromatography.

FIG. 10 is an SDS-PAGE electrophoregram for confirming purity.

FIG. 11 is a diagram representing optimal pH.

FIG. 12 is a diagram representing optimal temperature range.

FIG. 13 is a diagram representing stable pH range.

FIG. 14 is a diagram representing stable temperature range.

FIG. 15 is a diagram representing the relationship between electrophoresis distance and molecular weight.

FIG. 16 is a diagram representing the relationship between molecular weight and the plotted traveled distance of a standard protein.

FIG. 17 is a diagram representing the result of an AgM30 bacterial strain DPE gene product analysis performed with an *Escherichia coli* expression system.

FIG. 18 is diagram representing the result of an AgM30 bacterial strain DPE gene product analysis performed with an *Escherichia coli* expression system (pQE vector).

DESCRIPTION OF EMBODIMENTS

The present invention is concerned with a ketose 3-epimerase obtainable from microorganisms of the genus *Arthrobacter*, and having the substrate specificity described below. The ketose 3-epimerase of the present invention is characterized by the safety of the bacteria usable in food industry, low optimal pH, heat stability, and metal requirement.

[Safety]

The most notable feature of the present enzyme and *Arthrobacter globiformis* used for food industry is the safety of the bacteria. This bacterial strain is listed under "Glucose Isomerase from Immobilized *Arthrobacter globiformis*" in the FDA's EAFUS (Everything Added to Food in the United States): A Food Additive Database (US). The fact that the bacteria are directly immobilized in the method described in this database is a proof that the safety of the bacteria itself is very high indeed.

In Europe, use of the bacteria is described in "citrus fermentation to remove limonin and reduce bitterness" in the "Inventory of Microorganisms with a Documented History of Use in Food" published by EFFCA (The European food & feed cultures association) and IFD (International Federation for the Roofing Trade). This is suggestive of the foregoing bacterial strain being actually used for fermentation the same as yeasts, etc., and being very safe. The Food Additive List published in Japan lists *Arthrobacter* as the origin for enzymes such as α-amylase, isomaltodextranase, invertase, urease, glucanase, α-glucosyltransferase, and fructosyltransferase, and as the producer of trehalose or vitamin K (menaquinone).

It is rather surprising that no one has found an epimerase enzyme using this bacterial strain despite its long use in Japan, US, and Europe.

Enzymes, which are known as D-psicose producing enzymes, are from the genus *Pseudomonas*, the genus *Agrobacterium*, and the genus *Rhizobium*, etc. These are not listed in any of the American and European lists. There are reports of these bacteria being opportunistic pathogens, and infecting plant cells.

Many bacterial strains (60 or more strains) have been reported in fructose production from glucose with glucose isomerase, a representative glycoenzyme. However, only a handful of these bacteria, including the genus *Streptomyces*, the genus *Bacillus*, and the genus *Actinoplanes*, and *Arthrobacter* have actually been put to practical applications. Indeed, *Arthrobacter* represent highly safe bacterial strains used for food for many years.

[Optimal pH and Metal Requirement]

Other features of the present invention include the following.

The optimal pH of D-psicose producing bacteria is 7 to 9 for the genus *Pseudomonas*, 9 to 9.5 for the genus *Rhizobium*, and 7 to 8 for the genus *Agrobacterium*. On the other hand, the optimal pH range of the enzyme produced by the present bacterial strain is 6 to 8, and D-psicose production is possible also in a less coloring pH range of 7 or less.

There is a report based on 30-min enzyme activity measurement that activity increased in the presence of $Mn^{2+}$ and $Mg^{2+}$ in the genus *Rhizobium*, and in the presence of $Co^{2+}$ and $Mn^{2+}$ in the genus *Agrobacterium*. The present enzyme has been shown to increase activity in the presence of $Mn^{2+}$ or $Co^{2+}$. Because the activity also increases in the presence of $Mg^{2+}$ and $Ca^{2+}$, the present bacterial strain can be used to produce D-psicose with $Mg^{2+}$ and other metal ions.

[Origin and Identification of Bacterial Strain]

The present inventors isolated large numbers of bacterial strains, and found an M30 strain producing a novel ketose 3-epimerase. The M30 strain has been found to belong to the genus *Arthrobacter globiformis* after a phyloanalysis based on 16S rRNA gene base sequence homology.

Identification of Bacterial Strain (1) 16S rRNA Gene Base Sequence Homology

Analysis of the 16S rRNA gene region specified 734 bases.

(2) Homology Search

A homology search (BLAST search; Japan DNA Databank) was conducted for the 16S rRNA gene base sequence of the bacterial strain, using known bacterial strains. The search identified the M30 strain as an *Arthrobacter globiformis* from the name of the bacterial strain that had 97% or greater homology against the specified 734-base sequence, and the homology (%) value.

The *Arthrobacter globiformis* as the M30 bacterial strain having ketose 3-epimerase activity of the present invention has been deposited in the NITE Patent Microorganisms Depositary (Jun. 22, 2011; 2-5-8 Kazusa Kamatari, Kisarazu, Chiba) under the receipt number NITE AP-1111 and the accession number NITE P-1111.

As used herein, "ketose" means a hexose with a ketose structure, specifically fructose, psicose, tagatose, and sorbose, and "D- or L-ketose" means D- or L-forms of such sugars.

The ketose 3-epimerase of the present invention has activity to epimerize a D- or L-ketose at position 3 and produce a corresponding D- or L-ketose, and catalyzes the mutual conversion of D- or L-fructose and D- or L-psicose, and the mutual conversion of D- or L-tagatose and D- or L-sorbose. The ketose 3-epimerase of the present invention has the highest substrate specificity for D-fructose and D-psicose among D- and L-ketoses. The enzyme of the present invention can be obtained from microorganisms of the genus *Arthrobacter* (described later).

The ketose 3-epimerase of the present invention can be prepared by culturing an *Arthrobacter* microorganism having a ketose 3-epimerase production capability, and collecting the ketose 3-epimerase from the bacteria grown in the culture medium. Examples of the *Arthrobacter* microorganism advantageous for use include an *Arthrobacter globiformis* M30 (accession number NITE BP-1111) strain, and mutant strains thereof. The M30 strain has a relatively high ketose 3-epimerase production capability, and is preferred for obtaining the enzyme of the present invention. The M30 strain was originally deposited at the NITE International Patent Organism Depositary (NITE P-1111; Jun. 22, 2011; 2-5-8 higashi-Kazusa Kamatari, Kisarazu, Chiba, Japan), and transferred to the international depositary under the Budapest Treaty upon filing a request (May 2, 2012). The M30 strain has been internationally deposited with the accession number NITE BP-1111.

[Physical and Chemical Properties of the Present Enzyme Before Purification]

The activity of the ketose 3-epimerase enzyme before purification may be measured by measuring the amount of D-psicose produced with a D-fructose substrate. Specifically, an enzyme reaction mixture composition containing 50 mM tris-HCl buffer (pH 7.0; 200 ml), 0.2 M D-fructose (375 μl), enzyme liquid (100 μl), and 10 mM manganese chloride (75 μl) is allowed to react at 55° C. for 30 min, and the reaction is quenched by boiling the mixture for 2 min. The resulting liquid composition is then measured by HPLC. One unit of enzyme activity is defined as the amount of enzyme that epimerizes D-fructose and then produces 1 μmol of D-psicose per minute under the foregoing conditions. The enzyme unit for the epimerization of D-psicose to D-fructose in the reverse reaction is defined in the same manner through measurement performed under the same conditions.

The ketose 3-epimerase of the present invention may have the following physical and chemical properties.

(a) optimal pH:
6.0 to 10 under 55° C., 30-min reaction conditions in the presence of 1 mM divalent cobalt ions ($Co^{2+}$);

(b) optimal temperature:
about 50 to about 70° C. under pH 7.0, 30-min reaction conditions in the presence of 1 mM divalent cobalt ions ($Co^{2+}$);

(c) pH stability:
stable in at least a pH range of 5.5 to 11 under 4° C., 24-hour maintained conditions;

(d) heat stability:
stable at about 70° C. or less under pH 7.0, 10-min maintained conditions in the presence of 1 mM divalent cobalt ions ($Co^{2+}$), and stable at about 60° C. or less in the absence of 1 mM divalent cobalt ions ($Co^{2+}$); and (e) metal ion activation:
activatable by divalent manganese ions ($Mn^{2+}$) or divalent cobalt ions ($Co^{2+}$).

The ketose conversion reaction is typically performed under the following conditions.

Substrate concentration: 1 to 60% (w/v), desirably about 5 to 50% (w/v)

Reaction temperature: 10 to 70° C., desirably about 30 to 60° C.

Reaction pH: 5 to 10, desirably about 7 to 10

Enzyme activity: 1 unit or more per gram of substrate, desirably selected from 50 to 5,000 units.

Reaction time may be appropriately selected. However, considering economic efficiency, reaction time is typically 5 to 50 hours in the case of a batch reaction.

The reaction solution obtained by the conversion contains the raw material ketose and a newly produced ketose, and may be advantageously used directly as a sweetener, a humectant, a crystallization inhibitor, a shine-imparting agent, or the like. Typically, the reaction solution is decolored with activated carbon, desalted with H-type and OH-type ion conversion resins, and concentrated to produce a syrup-like product according to an ordinary method.

The newly produced ketose and the raw material ketose in the concentrate may be separated and purified, as required, by, for example, column chromatography that uses an alkali metal or alkaline earth metal strongly acidic cation exchange resin, and the fraction rich in the newly produced ketose may be concentrated to advantageously produce a syrup-like product. In the case of a crystallizable ketose, the ketose may be crystallized to advantageously obtain a crystalline product. Further, the separated raw material ketose may be advantageously reused as the raw material of another conversion reaction.

The ketoses obtained as above are preferable as sweeteners, and may be advantageously used as sweeteners or palatability improvers in various orally ingested products, including food and drinks, feed, bait, toothpastes, oral pastils, sublingual tablets, and oral medicine, and so on. The ketoses may also be advantageously used, for example, as a fermentation carbon source, a reagent, or a raw material or an intermediate of chemicals and drugs.

The present invention is described below in greater detail using experiments. The term "ketose 3-epimerase activity" used in the experiments below is the D-psicose 3-epimerase activity for the conversion of D-psicose to D-fructose as measured by the activity measurement method described above.

The present invention encompasses not only the ketose 3-epimerase encoded by the base sequence represented by SEQ ID NO: 2 or SEQ ID NO: 3 of the Sequence Listing, and that epimerizes position 3 of D- or L-ketose, and produces a corresponding D- or L-ketose, but a ketose 3-epimerase encoded by the base sequence represented by SEQ ID NO: 2 or SEQ ID NO: 3 of the Sequence Listing with the deletion, substitution, or addition of one or more bases that retains the activity of the encoded enzyme, or by a complementary base sequence thereof, and that epimerizes position 3 of D- or L-ketose, and produces a corresponding D- or L-ketose.

Experiment 1: *Arthrobacter globiformis* M30 (Accession Number NITE BP-1111) Strain Culture A seed culture medium 1% (v/v) of the *Arthrobacter globiformis* M30 (accession number NITE BP-1111) strain was aseptically added to an inorganic salt medium that contained 0.2% D-psicose as a carbon source, and ammonium sulfate as a nitrogen source. The bacteria were cultured at 30° C. for 16 hours while being agitated under aerated conditions. The ketose 3-epimerase activity in the resulting culture medium was about 14 units/100 ml culture medium.

Experiment 2: *Arthrobacter globiformis* M30 (Accession Number NITE BP-1111) Strain Culture and Extraction of Crude Enzyme The bacteria were harvested from the culture medium by centrifugation. The harvested bacteria were washed with 1 mM tris-HCl buffer (pH 7.0). The bacteria were then suspended in 10 ml of 1 mM tris-HCl buffer (pH 7.0), and the bacterial suspension was disrupted with an ultrasonic homogenizer (SONICS & MATERIALS) while being cooled in ice-cold water. The disrupted cells were centrifuged at 12,000 rpm for 20 min, and the supernatant was obtained as crude enzyme.

Experiment 3: Dialysis of Crude Enzyme

The crude enzyme was placed in a Cellulose Ester Dialysis Membrane (SPECTRUM Laboratory), and the whole membrane was immersed in a 20 mM EDTA-containing 10 mM tris-HCl buffer for 12 hours for dialysis. The membrane was washed twice with 10 mM tris-HCl (pH 7.0) buffer, and a crude enzyme liquid was removed from the membrane.

Experiment 4: Enzyme Activity Detection

A reaction was allowed under the reaction conditions below. After quenching the reaction by boiling, the reaction liquid was desalted with an ion-exchange resin, and filtered to prepare an HPLC sample. The sample was analyzed by chromatography using CK08EC (Mitsubishi Chemical Corporation) in an HPLC system (Tosoh). Each product sugar was determined by calculations from the peak area values of the chromatogram.

Test Results

Experiment 5: Properties of Ketose 3-Epimerase

1. Effects of Carbon Source and Carbon Source Concentration on Activity

The *Arthrobacter globiformis* M30 (accession number NITE BP-1111) strain was cultured in MSM media that contained 0.05 to 1% D-psicose (D-p), 1% D-fructose (D-f), 1% D-tagatose (D-t), 0.1% fructose (D-f), 0.1% D-psicose (D-p), 1% D-psicose (D-p), and 0.1% D-tagatose (D-t). The activity of each crude enzyme was then examined in the same manner as above.

Because the enzyme of the present bacteria was produced in the presence of D-psicose, the enzyme was found to be an enzyme induced by D-psicose, and the activity was the highest when the D-psicose concentration was 0.2% (FIG. 1).

2. Effects of Media on Enzyme Activity

The bacteria were cultured in three different media (minimum inorganic salt (MSM) medium, TSB medium, and yeast extract (YE) medium) at 30° C. for 16 hours, and crude enzymes were obtained in the same manner as above.

The enzyme activity was the highest when D-psicose was added to the minimum inorganic salt medium, which is the least expensive (FIG. 2).

3. Effects of Metal Ions on D-PE Activity

Enzyme activity was measured under the reaction conditions shown in Table 1 below, using the enzyme liquid dialyzed against EDTA-containing buffer in Experiment 3. The results are presented in FIG. 3.

The quenched activity by the dialysis against EDTA suggests that the present enzyme requires metal ions. Enzyme activity increased by addition of $MnCl_2$ and $CoCl_2$ in the measurement performed to examine the effect of metal ions on enzyme activity. This confirmed that the present enzyme requires $Mn^{2+}$ or $Co^{2+}$.

TABLE 1

| Reaction conditions | |
|---|---|
| 50 mM Tris-HCl buffer (pH 7.0) | 200 µl |
| 0.2M D-fructose (substrate) | 375 µl |
| Dialyzed crude enzyme | 100 µl |
| 10 mM metal salt | 75 µl |
| Reaction temperature | 55° C. |
| Reaction time | 30 min |

4. Effects of Temperature on D-PE Activity (Optimal Temperature)

Reactions were performed at various temperatures in a 10 to 80° C. range. The reaction conditions used to find the optimal temperature are presented in Table 2. The measurement results are shown in FIG. 4. The optimal temperature existed in the 50° C. to 70° C. temperature range.

TABLE 2

| Reaction conditions | |
|---|---|
| 50 mM Tris-HCl buffer (pH 7.0) | 200 µl |
| 0.2M D-fructose (substrate) | 375 µl |
| Crude enzyme | 100 µl |
| 10 mM $CoCl_2$ | 75 µl |
| Reaction temperature | 10 to 80° C. |
| Reaction time | 30 min |

5. Effects of Temperature on D-PE Activity (Heat Stability)

Heat stability was examined in the presence and absence of cobalt ions. A heat treatment was performed in pH 7.0, 10 to 80° C. conditions for 10 min in the presence of 1 mM cobalt ions, and the remaining activity was measured. The results are shown in FIG. 5. As shown in the figure, the enzyme was stable up to 70° C. in the presence of cobalt ions, and up to 60° C. in the absence of cobalt ions.

6. Effects of pH on D-PE Activity (Optimal pH)

Enzyme reactions were performed at various pH values to determine the optimal reaction pH. The following buffers were used in different pH ranges.

pH 3 to 6: 50 mM citrate buffer pH 6.0 to 8.0: 50 mM phosphate buffer pH 7.0 to 9.0: tris-HCl buffer pH 9.0 to 11.0: glycine-sodium hydroxide buffer Reaction conditions are presented in Table 3. The results are shown in FIG. 6. The optimal pH range was found to be 6 to 10.

TABLE 3

Reaction conditions

| | |
|---|---|
| 50 mM buffer (pH 8.0 to 11.0) | 200 µl |
| 0.2M D-fructose | 375 µl |
| Crude enzyme | 100 µl |
| 10 mM CoCl$_2$ | 75 µl |
| Reaction temperature | 55° C. |
| Reaction time | 30 min |

7. Effects of pH on D-PE Activity (pH Stability)

The enzyme was maintained at 4° C. for 24 hours at each pH, and the remaining enzyme activity was determined after a 55° C., 30-min reaction. The results are shown in FIG. 7. The present enzyme had pH stability in a wide pH range of about 6 to 11.

8. D-PE Substrate Specificity

Eight hexose (ketoses) were used to examine the substrate specificity of the present enzyme before purification. An enzyme reaction composition (Table 4) containing each substrate (0.2 M, 350 µl) and an enzyme liquid (350 µl; Tris buffer pH 7.0) was allowed to react at 55° C. for 30 min, and the ketose epimerized and produced from each sugar was analyzed by HPLC. The results are presented as relative activity for each ketose relative to the D-psicose epimerization activity which is taken as 100, as follows. Table 5 presents relative activity values for D-fructose, D-psicose, D-sorbose, D-tagatose, L-fructose, L-psicose, L-sorbose, D-tagatose, L-fructose, L-psico, and L-tagatose substrates. The activity was the highest for D-psicose, and the second highest for D-fructose. The substrate specificity can be said as characteristic of the D-psicose 3 epimerase (DPE), not other free ketose 3 epimerases, and was clearly different from the specificity of the D-tagatose3-epimerase (DTE) of *Pseudomonas cichorii*.

TABLE 4

Reaction conditions

| | |
|---|---|
| Substrate (0.2M hexose, see below) | 350 µl |
| Crude enzyme | 350 µl |
| Temperature | 55° C. |
| Reaction time | 30 min |

TABLE 5

| Substrate | Relative activity (%) |
|---|---|
| D-fructose | 58.14 |
| D-psicose | 100* |
| D-sorbose | 1.25 |
| D-tagatose | 5.42 |
| L-fructose | 12 |
| L-psicose | 12 |
| L-sorbose | 8 |
| L-tagatose | 12.5 |

[Enzyme Purification and Measurement of Physical and Chemical Properties]

The enzyme of the present invention was further purified, and the enzyme in the further purified state was measured for physical and chemical properties.

[Enzyme Activity Measurements During and after Purification, and Protein Measurement]

Enzyme activity was measured by performing an enzyme reaction with the enzyme reaction mixture composition shown in Table 6. The enzyme reaction was performed at 30° C. for 30 min, and the amount of the enzyme that produced 1 micromole of D-fructose in 1 min under these conditions was taken as one unit. After the reaction, the reaction mixture was put in a boiling liquid for 3 min to quench the reaction. After deionization, the product D-fructose was measured by HPLC analysis. Protein measurement was performed by using the Bradford method, using 5 µL of the enzyme liquid added to a Bradford solution (250 µl) and evenly stirred therein.

TABLE 6

Composition of enzyme reaction mixture

| | |
|---|---|
| Enzyme liquid | 40 µl |
| 10 mM Tris-HCl pH 7.5 | 160 µl |
| 20 mM MgCl$_2$ | 100 µl |
| 400 mM D-psicose | 100 µl |

The purified enzyme was found to be an epimerase of a homotetramer structure that had a subunit molecular weight of about 32 kDa as measured by SDS-PAGE, and a molecular weight of 120 kDa as measured by gel filtration.

[Bacteria Culture]

[Preculture]

The present bacteria were precultured by being inoculated to the medium shown in Table 7. The medium (100 ml) was put in a 500-ml Erlenmeyer flask, and shake cultured at 30° C. and 200 rpm for 12 hours.

TABLE 7

Medium composition

| | |
|---|---|
| (NH$_4$)$_2$SO$_4$ | 0.26% |
| KH$_2$PO$_4$ | 0.24% |
| K$_2$HPO$_4$ | 0.56% |
| MgSO$_4$•7H$_2$O | 0.01% |
| Yeast extract | 0.05% |
| D-psicose | 0.5% |

[Main Culture]

The preculture growth medium (100 mL) was inoculated to the main culture (10 L) shown in Table 8, and cultured at 30° C. for 24 hours under aerated (2 ml/min) and stirred (300 rpm) conditions.

TABLE 8

Main culture

| | |
|---|---|
| (NH$_4$)$_2$SO$_4$ | 0.52% |
| KH$_2$PO$_4$ | 0.24% |
| K$_2$HPO$_4$ | 0.56% |
| MgSO$_4$•7H$_2$O | 0.03% |
| Citric acid | 0.2% |
| Yeast extract | 0.1% |
| D-psicose | 0.5% |

[Enzyme Extraction]

Viable bacteria (230 g) were obtained from the main culture (10 L). The bacteria were suspended in 1 l of a buffer (10 mM Tris-HCl pH 7.5+1 mM $MgCl_2$), and disrupted with a high-pressure homogenizer to extract the enzyme. The disruption was conducted at 20,000 psi. The insoluble matter was removed by centrifugation (10,000 rpm, 20 min, 4° C.) to obtain a crude enzyme liquid (1,150 ml). The crude enzyme liquid (130 ml) was used for enzyme purification.

[Enzyme Purification]
[PEG (Polyethylene Glycol) Fractionation]

PEG 6000 (26 g; concentration 20%) was added to the crude enzyme liquid (130 ml), and dissolved therein by being stirred at low temperature. The resulting precipitate and the supernatant were separated from each other by centrifugation (10,000 rpm, 20 min, 4° C.). The precipitate was dissolved in 30 mL of a buffer. Activity measurement revealed that there was no activity in the precipitate. Thereafter, PEG (26 g; final concentration 40%) was added to the supernatant, and the resulting precipitate was separated from the supernatant. Activity measurement revealed activity in the supernatant, but not in the precipitate.

[PEG Removal Method]

The enzyme did not precipitate, and was present in the supernatant even at 40% PEG concentration. PEG needs to be removed for the subsequent purification of the supernatant enzyme. PEG was removed by taking advantage of the non-adsorbing property of PEG against an ion-exchange resin. Specifically, the enzyme was adsorbed to anion-exchange resin, and the PEG was washed away. The adsorbed enzyme was then eluted from the resin with high-concentration NaCl. The PEG was removed in this manner.

Specifically, the PEG was removed as follows.

An enzyme liquid containing 40% PEG was put in a Q-Sepharose Fast Flow (58 ml) equilibrated with a buffer (10 mM Tris-HCl pH 7.5+10 mM $MgCl_2$), and the mixture was gently stirred for 10 min to adsorb the enzyme. The resin was packed into a column (about 50 ml volume), and the enzyme was eluted with 150 ml of a buffer (1 M NaCl+10 mM Tris-HCl pH 7.5+10 mM $MgCl_2$). The eluate was fractionated in 10-ml portions, and fractions with activity were collected. The fractions with activity were dialyzed overnight against a buffer (10 mM Tris-HCl pH 7.5+10 mM $MgCl_2$) to remove NaCl and obtain a PEG fractionated enzyme liquid.

[Purification by Ion-Exchange Chromatography]

The PEG fractionated enzyme liquid was purified by ion chromatography separation. By using a Q-Sepharose High Performance column in an AKTA system, the sample was fractionated into 5-ml fractions with 35% to 60% concentration gradient of 1 M NaCl at a flow rate of 1.5 ml/min. Enzyme activity was detected in the fractions indicated by arrow in FIG. 8. These fractions were collected, and an enzyme purified by ion exchange chromatography separation was obtained. FIG. 8 is an elution diagram based on ion exchange chromatography separation. Enzyme activity appeared as indicated by arrow at the central portion of the protein elution represented in FIG. 8, and these fractions were collected.

The enzyme purified by ion exchange chromatography separation was further purified by hydrophobic chromatography separation. A RESOURCE PHE column (6 ml) was used. Ammonium sulfate (2 M) was added and dissolved in the enzyme liquid. The sample was eluted into 5-mL fractions with 2 M ammonium sulfate concentration being decreased from 100% to 0% at a flow rate of 3 ml/min. Enzyme activity was detected in the eluates that appeared as large peaks of the arrow in FIG. 9. These fractions were dialyzed to remove ammonium sulfate, and an enzyme purified by hydrophobic chromatography separation was obtained. Activity appeared in the second large peak of the protein elution. The arrow in FIG. 9 indicates the collected fractions.

[Purification Table]

Table 9 below summarizes information concerning the enzyme purification process, including the protein amount and the enzyme activity of the crude enzyme, the PEG fractionated enzyme, the enzyme purified by ion exchange chromatography separation, and the enzyme purified by hydrophobic chromatography. The purification produced the purified enzyme at a yield of 12% with a purification factor of 31.5.

TABLE 9

| Purification step | Volume (ml) | Protein concentration (μg/ml) | Total protein amount (mg) | Relative activity (U/mg) | Total activity (U) | Yield (%) | Purification factor |
|---|---|---|---|---|---|---|---|
| Crude enzyme | 130 | 3457 | 450.0 | 2.24 | 1006 | 100 | 1 |
| After PEG fractionation | 48.0 | 1702 | 81.7 | 5.74 | 469 | 47 | 2.6 |
| Q-Sepharose | 14.8 | 259 | 3.84 | 62.1 | 238 | 24 | 27.7 |
| Re-phenyl | 7.4 | 222 | 1.65 | 70.5 | 116 | 12 | 31.5 |

[Purity of Purified Enzyme]

The purity of the purified enzyme was confirmed by SDS PAGE (gel concentration 15%) using an ordinary method. In FIG. 10, the left lane represents the standard protein, and the second lane is of the enzyme purified by hydrophobic chromatography. Single bands were confirmed between 29 to 45 kDa. The result thus confirmed clean enzyme purification.

[Properties of Purified Enzyme]

The properties of the purified enzyme were examined.

[Optimal Reaction pH]

As shown in FIG. 11, activity was found in pH 6 to 11, and the highest activity occurred at pH 7.5.

For the optimal reaction pH measurement, a reaction was allowed at 30° C. for 30 min with various buffers of pH 4 to 11, using D-psicose as the substrate. The product D-fructose was then measured by HPLC. Table 10 shows the reaction mixture composition used. The buffers used are presented in Table 11.

TABLE 10

| Reaction mixture composition | |
|---|---|
| Enzyme liquid | 40 µl |
| 50 mM buffer of each pH | 160 µl |
| 20 mM MgCl$_2$ | 100 µl |
| 400 mM D-psicose | 100 µl |

TABLE 11

| Buffers used | |
|---|---|
| pH 4, 5, 6 | Citrate |
| pH 6, 7, 8 | Na-phosphate |
| pH 7.5, 8, 9 | Tris-HCl |
| pH 9, 10, 11 | Glycine-NaOH |

[Optimal Reaction Temperature]

It was found from FIG. 12 representing the results of reaction temperature and relative activity measurements that the optimal temperature of the present enzyme was 70° C. with addition of Mg$^{2+}$ ions. The optimal temperature was 60° in the absence of Mg$^{2+}$ ions. In the presence of Mg$^{2+}$ ions, the optimal temperature increased abruptly, and high activity was observed in a temperature range of 60° C. to 80° C. The relative activity values shown in FIG. 12 are relative to the highest activity, which is taken as 100, that occurred in the presence of Mg$^{2+}$ ions at 70° C. The reaction conditions are as presented in Table 12. Specifically, a reaction was allowed for 30 min with the purified enzyme at pH 7.5 at each temperature, and the amount of the product D-fructose was measured. Assessment was made with addition of Mg$^{2+}$ ions, and without Mg$^{2+}$ ions (water was added instead of MgCl$_2$). The reaction was performed for 30 min at 20, 30, 40, 50, 60, 70, 80, 90, and 100° C.

TABLE 12

| Reaction mixture composition and reaction conditions | |
|---|---|
| Enzyme liquid | 40 µl |
| 10 mM Tris-HCl pH 7.5 | 160 µl |
| 20 mM MgCl$_2$ | 100 µl |
| 400 mM D-psicose | 100 µl |

[pH Stability]

The pH stability of the purified enzyme was examined. The purified enzyme was stable in the pH range of 5 to 11, as shown by the result represented in FIG. 13.

The measurement was made under the maintained 4° C., 24-hour conditions at each pH, and an enzyme reaction was allowed at pH 7.5. The remaining activity was measured at 30° C. for 30 min, at pH 7.5. The same buffers used for the optimal pH measurement were used.

The remaining activity values at each pH shown in FIG. 13 are relative to the remaining activity with the citrate buffer at pH 6 which is taken as 100.

[Heat Stability]

The heat stability of the purified enzyme was examined in the presence and absence of Mg$^{2+}$ ions. The heat stability greatly differed in the presence and absence of Mg$^{2+}$ ions, and the Mg$^{2+}$ ions increased the enzyme heat stability. The enzyme remained stable at 50° C. for 1 hour in the presence of Mg$^{2+}$ ions. On the other hand, the heat stability was overall about 10° C. lower in the absence of Mg$^{2+}$ ions. These results, combined with the optimal reaction temperature of 70° C., suggest that the stability of the present enzyme increases in the presence of the substrate. Specifically, the results appear to indicate high stability of the ES complex. FIG. 14 shows the relative activity values relative to the activity of the enzyme without heat treatment which is taken as 100.

The heat treatment was performed under the following conditions. A 300-µl mixture containing a purified enzyme liquid (40 µl), a buffer (10 mM Tris-HCl pH 7.5; 160 µl), 4 mM MgCl$_2$ (100 µl; water when Mg$^{2+}$ ions were not added) was maintained for 1 hour at each temperature, and cooled in ice-cold water for 10 min. The remaining enzyme activity was then measured according to an ordinary method.

[Effects of Metal Ions]

The enzyme was examined for metal ion requirement. The purified enzyme was dialyzed for 2 hours against 10 mM Tris-HCl containing 1 mM EDTA (pH 7.5). The enzyme was further dialyzed against an EDTA-free 10 mM Tris-HCl buffer (pH 7.5) for a whole day and night to obtain an EDTA treated enzyme. This enzyme was used to measure the effect of metal ions on enzyme activity, using 1 mM of various metal ions, and D-psicose as the substrate. The results are presented in Table 13, in which the activity with addition of each type of metal ions is shown as the relative value with respect to the activity of the enzyme without metal ions which is taken as 100.

The activity increased 1.3-fold or greater in the presence of Mg$^{2+}$, Co$^{2+}$, or Mn$^{2+}$ ions, and the highest activity was observed in the presence of Mg$^{2+}$ ions. The result thus demonstrated that the present enzyme was activated by Mg$^{2+}$ ions. Considering the large effect of Mg$^{2+}$ ions on heat stability, Mg$^{2+}$ ions were found to be important for the reaction of the present enzyme.

TABLE 13

| Metal ion | Relative activity (%) |
|---|---|
| Co$^{2+}$ | 130 |
| Mn$^{2+}$ | 137 |
| Mg$^{2+}$ | 150 |
| Ca$^{2+}$ | 110 |
| Ni$^{2+}$ | 87 |
| Fe$^{2+}$ | 32 |
| Zn$^{2+}$ | 0 |
| Cu$^{2+}$ | 0 |
| K$^+$ | 117 |
| Na$^+$ | 120 |
| None | 100 |

[Substrate Specificity]

The reactivity of the present enzyme was examined with respect to the all ketohexoses. The reaction mixture composition is shown in Table 14. The enzyme activity was tabulated as the relative activity with respect to the activity for D-psicose which is taken as 100. The present enzyme had activity for the all ketohexoses, and the activity was the highest for D-psicose. This clearly demonstrated that the enzyme was a D-psicose 3-epimerase. The substrate specificity is summarized in Table 15. The initial velocity was determined by allowing a reaction at 70° C. for 120 min for D-sorbose and L-fructose, and 70° C. for 20 min for the other substrates.

TABLE 14

| Reaction mixture composition | |
|---|---|
| Enzyme liquid | 100 µl |
| Buffer | 100 µl |

TABLE 14-continued

| Reaction mixture composition | |
| --- | --- |
| 20 mM MgCl$_2$ | 100 µl |
| 400 mM substrate | 100 µl |
| | 400 µl |

TABLE 15

| Substrate | Relative activity (%) |
| --- | --- |
| D-psicose | 100 |
| D-fructose | 43.8 |
| L-tagatose | 44.0 |
| L-psicose | 21.2 |
| D-tagatose | 18.3 |
| L-sorbose | 16.6 |
| D-sorbose | 1.13 |
| L-fructose | 0.97 |

[Km and Vmax]

The Km and Vmax of the present enzyme for D-psicose and D-fructose were measured. The measurement was made by measuring enzyme activity at 30° C. in the presence of Mg$^{2+}$ ions. The enzyme had $V_{max}$=168 U/mg and $K_m$=30.1 mM for D-psicose, and $V_{max}$=68.5 U/mg and $K_m$=31.5 mM for D-fructose.

[Enzyme Molecular Weight]
[Subunit Molecular Weight]

SDS-PAGE (15% gel concentration) was performed for the purified enzyme and molecular weight markers, and the distances traveled by these molecules were measured. The subunit molecular weight of the present enzyme was found to be about 32 kDa.

FIG. 15 represents the relationship between electrophoresis distance and molecular weight. In FIG. 15, the electrophoresis distance (cm) of a marker protein is plotted against molecular weight (kDa). From the distance of about 4.1 cm traveled by the purified enzyme, the subunit of the present enzyme was estimated to be about 32 kDa. The electrophoregram is shown in FIG. 10.

[Enzyme Molecular Weight]

The molecular weight of the present enzyme was measured by gel filtration chromatography. Specifically, the relationship between a standard protein and traveled distance was determined (FIG. 16), and the molecular weight was found from the traveled distance of the present enzyme. The enzyme molecular weight was found to be about 120 kDa.

A Superdex 200 pg 16/600 column was used for the molecular weight measurement by gel filtration chromatography. The running buffer composition contained 10 mM Tris-HCl (pH 7.5), NaCl (200 mM), and MgCl$_2$ (1 mM).

The following five standard proteins (markers) were used.

| (1) Ovalbumin | MW: 44,000 |
| --- | --- |
| (2) Conalbumin | 75,000 |
| (3) Aldolase | 158,000 |
| (4) Ferritin | 440,000 |
| (5) Tyroglobulin | 669,000 |

The present enzyme had an elution volume of 72.5 ml, and the molecular weight of the present enzyme was found to be about 120 kDa from calculations based on the relationship between traveled distance and molecular weight. From the subunit molecular weight of about 32 kDa found by SDS-PAGE, and the molecular weight of about 120 kDa the present enzyme found by gel filtration, the present enzyme is believed to have a homotetramer structure with a subunit molecular weight of 32 kDa.

[Comparison with Other DPE and DTE]

Table 16 summarizes the properties of D-tagatose 3-epimerases and D-psicose 3-epimerases reported to date. A notable feature of the enzyme produced by the present bacterial strain compared to the ketohexose 3-epimerases originating in other microorganisms is the higher optimal temperature.

TABLE 16

| | Strain for enzyme source | | | | |
| --- | --- | --- | --- | --- | --- |
| | A. globiformis (DPE) | C. cellulolyticum (DPE) | A. tumefaciens (DPE) | P. cichorii (DTE) | R. sphaeroides (DTE) |
| Molecular mass (kDa) | 120 (tetramer) | | 132 (tetramer) | 68 (dimer) | 64 (dimer) |
| Optimal temperature (° C.) | 70 | 55 | 50 | 60 | 40 |
| Optimal pH | 7.5 | 8 | 8 | 7.5 | 9 |
| Metal required | Mg$^{2+}$ (Mn$^{2+}$, Co$^{2+}$) | Co$^{2+}$ | Mn$^{2+}$ | Mn$^{2+}$ | Mn$^{2+}$ |
| Substrate with highest specificity | D-Psicose | D-Psicose | D-Psicose | D-Tagatose | D-Fructose |
| Equilibrium ratio between D-fructose and D-psicose | 25:75 (40° C.) 30:70 (70° C.) | 32:68 (55° C.) | 32:68 (30° C.) 33:67 (40° C.) | 20:80 (30° C.) | 23:77 (40° C.) |

The ketose 3-epimerase of the present invention undergoes an isomerization reaction that does not require coenzyme, as with the case of other epimerases and isomerases. The enzyme can thus be used by being immobilized, and high-activity immobilized enzymes can be obtained by using various immobilization techniques. A continuous and large epimerization reaction is possible with such immobilized enzymes. Because the enzyme can be immobilized in industrial scale, mass production of the target ketose is possible.

[Putative Amino Acid Sequence of Purified Enzyme]

The amino acid sequence of the purified enzyme was analyzed. The purified enzyme protein (about 0.1 to 0.2 □g) was treated with trypsin, and the amino acid sequence of the fragment was analyzed with Ultraflxtreme MALDI-TOF MS (Bruker). The result is presented below as SEQ ID NO: 4 of the Sequence Listing.

```
                                                           [SEQ ID NO: 4]
MKILILGGTR  FLGRAFVEEA  LQRGHEVTLF  NRGTNKEIFP  EVEQLI GDRN       50

GDVSSLENRK  WDVVIDTCGF  SPHHIRNVGE  VLKDNIEHYI  FISSLSVYKD       100

WIPHHIKEDY  ILQPEPTGDQ  IKAVENGEIS  PYEHYGALKV  LCEKEAEKYW       150

PGRVLHVRAG  LLSGMFDYTD  RLPYWIGRVA  KGGKVLVPGR  KNRPVQIVDI       200

KDVANWGLNM  AENNKAGIFN  VTGPNYELTM  AGLLNTCKKV  TNSDAEFVWV       250

EESFMNEHKV  QPWTEMPLWL  PETISLEGET  KPWKGGFSIS  IESAVKEGLT       300

FRRLEETVTD  VYAWMKSVDE  WELKAGISGE  REKRLLENWY  Q                341
```
(G: glycine, A: alanine, V: valine, L: leucine, I: isoleucine, M: methionine, F: phenylalanine, W: triptophan, Y: tyrosine, P: proline, C: cysteine, E: glutamic acid, D: aspartic acid, Q: glutamine, N: asparagine, K: lycine, R: arginine, H: histidine, S: serine, T: threonine)

Example 1

The present microorganism was grown in a minimum inorganic salt medium supplemented with D-psicose as the carbon source, and the enzyme obtained from the grown bacteria was used to examine the equilibrium ratio of D-psicose and D-fructose. The reaction mixture composition used contained 50 mM Tris buffer (200 μl), 0.2 M D-psicose or D-fructose, enzyme liquid (100 μl), and 10 mM $CoCl_2$ (75 μl). The reaction was performed for 24 hours at a reaction temperature of 50° C. After the reaction, the D-fructose and D-psicose amounts in the reaction mixture were measured by HPLC.

The same equilibrium ratio was reached irrespective of whether D-psicose or D-fructose was used as the substrate.

D-psicose:D-fructose equilibrium ratio=27:73

The result indicates that a reaction using D-fructose can convert 27% of the D-fructose into D-psicose. This is the clear indication that production of D-psicose from D-fructose is indeed possible.

Example 2

The epimerization equilibrium between D-psicose and D-fructose was examined with the purified enzyme. The D-psicose:D-fructose ratio was 25:75 at 40° C., and 30:70 at 70° C. in the equilibrium state.

Example 3

Specifying DPE Gene Base Sequence Through Whole Genome Analysis of AgM30 Bacterial Strain The foregoing test results suggested that the DPE of the AgM30 bacterial strain are completely different from known DPEs, and cannot be isolated with PCR amplification techniques or existing protein database. To investigate, the whole genome sequence of the AgM30 bacterial strain was determined, and a protein database was constructed therefrom. Genomic DNA was isolated and purified from the AgM30 bacterial strain with the DNeasy Blood & Tissue kit (Qiagen), and 19.58 μg of the genomic DNA was sent to the Takara Bio's Dragon Genomics Center for high speed sequence analysis. As a result, 22 contigs of 4 kb or more were obtained in a total of 513569410 bp analyzed. The 22 contigs, with the length of about 5.1 Mb, were considered to be sufficient to cover the whole genome sequence of the *Arthrobacter globiformis* M30.

[Construction of AgM30 Bacterial Strain Protein Database]

4798 putative ORFs were found in the about 5.1 Mb gene sequence by using a GeneMark S program, and the amino acid sequence of each ORF was estimated. These 4798 amino acid sequences were used as an AgM30 bacterial strain protein database.

[Reidentification of Protein with AgM30 Bacterial Strain DPE Activity]

The protein database was submitted to the protein identification system MASCOT server (Matrix Science), and a protein that showed DPE activity was reidentified. The protein had 52% similarity in the underlined portions of the amino acid sequences in the following SEQ ID NO: 1 of the Sequence Listing. This result strongly suggested that the protein was the DPE of the AgM30 bacterial strain.

```
                                                      [SEQ ID NO: 1]
  1  MKIGCHGLVW  TGHFDAEGIR  YSVQKTREAG  FDLVEFPLMD  PFSFDVQTAK

51  SALAEHGLAA  SASLGLSDAT  DVSSEDPAVV  KAGEELLNRA  VDVLAELGAT

101  DFCGVIYSAM  KKYMEPATAA  GLANSKAAVG  RVADRASDLG  INVSLEVVNR

151  YETNVLNTGR  QALAYLEELN  RPNLGIHLDT  YHMNIEESDM  FSPILDTAEA

201  LRYVHIGESH  RGYLGTGSVD  FDTFFKALGR  IGYDGPVVFE  SFSSSVVAPD

251  LSRMLGIWRN  LWADNEELGA  HANAFIRDKL  TAIKTIELH
```

Sequence 2SEQ ID NO: 1: An amino acid sequence identified from the protein database of AgM30 bacterial strain. The underlined amino acid sequences matched the peaks obtained by MALDI-TOF MS.

[Isolation of DPE Gene from AgM30 Bacterial Strain]

Genomic gene information was acquired from the amino acid sequence, and amplification PCR primers (Ag1DPE_F: 5'-ATGAAAATTGGTTGCCATG-3', and Ag1DPE_R: 5'-TTAGTGCAGTTCGATGGT-3') were designed. The DPE gene was then amplified from the genome of the AgM30 bacterial strain. A sequence analysis of the PCR product found two gene base sequences: a gene sequence of 870 bp represented by the sequence 11 (SEQ ID NO: 2 of the Sequence Listing) below, and a gene sequence represented by sequence 12 (SEQ ID NO: 3 of the Sequence Listing) with a thymine (T) replacing the cytosine (C) at base 15 of sequence 11 (underlined).

[Sequence 3 (SEQ ID NO:) 2 of the Sequence Listing]

ATGAAAATTGGTTGCCATGGCCTGGTTTGGACCGGCCACTTCGACGCTG

AAGGCATTCGCTACTCCGTCCAGAAAACCAGGGAAGCCGGTTTCGACCT

CGTTGAGTTCCCGCTCATGGATCCGTTCTCCTTCGATGTGCAGACGCC

AAGTCCGCACTGGCCGAACATGGGCTGGCGGCCTCGGCATCTCTGGAC

TCTCGGACGCCACTGACGTAAGCAGCGAAGATCCCGCCGTCGTGAAGGC

AGGGGAGGAGCTGCTCAACCGCGCCGTGGATGTTCTGGCCGAACTGGGT

GCGACGGATTTCTGCGGCGTGATTTATAGCGCCATGAAGAAGTACATGG

AGCCGGCAACTGCTGCCGGGCTGGCCAACAGCAAGGCAGCCGTCGGGCG

GGTCGCGGACCGGGCATCGGATCTGGGGATCAATGTTTCGCTGGAGGTC

GTCAACAGGTACGAAACCAACGTACTGAACACCGGACGTCAGGCCCTTG

CCTACTTGGAGGAGCTCAACCGGCCGAACCTGGGCATCCACCTGGACAC

TTACCACATGAACATTGAGGAATCGGACATGTTCTCCCCGATCCTGGAC

ACCGCGGAGGCCCTGCGGTACGTCCATATCGGCGAAAGCCACCGCGGCT

ACCTCGGCACGGGAAGCGTTGACTTCGACACTTTCTTCAAGGCCCTCGG

CCGCATCGGCTATGACGGACCCGTTGTCTTCGAATCGTTCTCCTCCTCC

GTCGTGGCACCGGATCTGAGCCGGATGCTCGGCATCTGGCGCAACCTGT

GGGCCGACAACGAGGAACTGGGTGCGCACGCGAATGCCTTCATCCGCGA

CAAGCTCACCGCGATCAAGACCATCGAACTGCACTAA

Sequence 3 (SEQ ID NO: 2 of the Sequence Listing): a DPE gene sequence amplified from the genomic DNA of AgM30 bacterial strain.

[Sequence 4 (SEQ ID NO: 3 of the Sequence Listing)]

ATGAAAATTGGTTGTCATGGCCTGGTTTGGACCGGCCACTTCGACGCTG

AAGGCATTCGCTACTCCGTCCAGAAAACCAGGGAAGCCGGTTTCGACCT

CGTTGAGTTCCCGCTCATGGATCCGTTCTCCTTCGATGTGCAGACGCC

AAGTCCGCACTGGCCGAACATGGGCTGGCGGCCTCGGCATCTCTGGAC

TCTCGGACGCCACTGACGTAAGCAGCGAAGATCCCGCCGTCGTGAAGGC

AGGGGAGGAGCTGCTCAACCGCGCCGTGGATGTTCTGGCCGAACTGGGT

GCGACGGATTTCTGCGGCGTGATTTATAGCGCCATGAAGAAGTACATGG

AGCCGGCAACTGCTGCCGGGCTGGCCAACAGCAAGGCAGCCGTCGGGCG

GGTCGCGGACCGGGCATCGGATCTGGGGATCAATGTTTCGCTGGAGGTC

GTCAACAGGTACGAAACCAACGTACTGAACACCGGACGTCAGGCCCTTG

CCTACTTGGAGGAGCTCAACCGGCCGAACCTGGGCATCCACCTGGACAC

TTACCACATGAACATTGAGGAATCGGACATGTTCTCCCCGATCCTGGAC

ACCGCGGAGGCCCTGCGGTACGTCCATATCGGCGAAAGCCACCGCGGCT

ACCTCGGCACGGGAAGCGTTGACTTCGACACTTTCTTCAAGGCCCTCGG

-continued

CCGCATCGGCTATGACGGACCCGTTGTCTTCGAATCGTTCTCCTCCTCC

GTCGTGGCACCGGATCTGAGCCGGATGCTCGGCATCTGGCGCAACCTGT

GGGCCGACAACGAGGAACTGGGTGCGCACGCGAATGCCTTCATCCGCGA

CAAGCTCACCGCGATCAAGACCATCGAACTGCACTAA

Sequence 4: (SEQ ID NO: 3 of Sequence Listing): a DPE gene sequence amplified from the genomic DNA of AgM30 bacterial strain. The cytosine (C) at base 15 of sequence 11 is replaced with a thymine (T) (underlined).

[Analysis of DPE Gene Product by *Escherichia coli* Expression System]

An *Escherichia coli* expression system was constructed by using sequence 11 (SEQ ID NO: 2 of the Sequence Listing). The DPE gene of AgM30 bacterial strain origin was incorporated into a pET vector (Clontech), which was then used to transform *Escherichia coli* for expression. As a result, an inducible protein was confirmed in a soluble fraction, as shown in FIG. 17. DPE activity was also confirmed, but the activity per milliliter of culture was about the same as that of the wild type.

In order to improve activity in an *Escherichia coli* expression system, the DPE gene of AgM30 bacterial strain origin was incorporated into a pRSET vector (Invitrogen) and a pCold vector (Takara Bio) to create *Escherichia coli* transformants. The measured DPE activity per milliliter of culture was about the same as that of the wild type in the pRSET vector system, and was about 10 times greater than that of the wild type in the pCold vector system.

[Analysis of DPE Gene Product with *Bacillus subtilis* Expression System]

Analysis was performed by constructing a *Bacillus subtilis* system, which reportedly produces a higher yield of genetically recombinant protein than *Escherichia coli* systems. The DPE gene of AgM30 bacterial strain origin was incorporated into a pHT01 vector (MoBiTec) designed for transformation of the host *Bacillus subtilis*, and the vector was introduced to transform the host after sequence analysis. As a result, large numbers of transformants with the acquired antibiotic resistance were obtained. However, DPE gene production was not observed in a DPE gene induction experiment, and the activity was undetectable.

[Mass Production of DPE Gene Product with *Escherichia coli* Expression System]

Given the result that mass production of DPE gene products was not possible with the *Bacillus subtilis* system, an experiment was conducted to mass produce DPE gene products of AgM30 bacterial strain origin by using the *Escherichia coli* system. The vector systems formerly used add a His-tag at the N terminus, or a solubilization tag to facilitate easy purification of recombinant protein. Considering that these tags might affect the yield and the enzyme activity of the recombinant protein, a pQE vector (Qiagen) system was used that does not add tags to the recombinant protein. The DPE gene of AgM30 bacterial strain origin was incorporated into a pQE60 vector (Qiagen), and the host *Escherichia coli* M15 [pREP4] (Qiagen) was transformed. The expression product was then analyzed by SDS-PAGE (gel concentration 12%) electrophoresis. As shown in FIG. 18, the expression product protein was confirmed in a soluble fraction near about 30 kD, about the same molecular weight as that of the wild-type protein. The DPE enzyme activity per milliliter of culture was 55.2 U (μmol/min). This is about a 30- to 37-fold increase from the currently available enzyme activity 1.5 to 1.8 U (μmol/min per milliliter of culture) of the DPE coarsely purified from the *Arthrobacter globiformis* M30 bacterial strain.

INDUSTRIAL APPLICABILITY

The ketose 3-epimerase of the present invention acts on a free D- or L-ketose, or D- or L-ketopentose, and epimerizes these ketoses at position 3 to easily produce a corresponding D- or L-ketose, or D- or L-ketopentose. This reaction paves the way for the D-psicose mass production that uses various ketoses, particularly D-fructose as raw material. Further, the ketose 3-epimerase of the present invention can be used to obtain high-activity immobilized enzymes with the use of various immobilization techniques, and such immobilized enzymes can be used to perform a continuous and large epimerization reaction. Because the enzyme can be immobilized in industrial scale, mass production of the target ketose is possible.

The establishment of the ketose 3-epimerase of the present invention, and the method of production thereof is industrially highly significant not only in sugar production but in a variety of related fields, such as in production of food, cosmetics, and drugs.

The most notable advantage of using the present enzyme-producing *Arthrobacter globiformis* in food industry is the safety of the bacteria. The fact that this bacterial strain is listed in the FDA's EAFUS in the US is a proof that the safety of the bacteria itself is very high indeed. Enzymes produced by the genus *Pseudomonas*, the genus *Agrobacterium*, and the genus *Rhizobium* are examples of known D-psicose producing enzymes. These are not contained in any of the American and European lists, and there are reports of these bacteria being opportunistic pathogens, and infecting plant cells. It has thus been indeed very laborious to check the safety of these microorganisms. Being able to use bacteria that are very safe by themselves as in the present invention is a large technological improvement.

The invention claimed is:

1. A recombinant expression vector comprising a DNA encoding ketose 3-epimerase having the following substrate specificities (A) and (B):
   (A) substrate specificity whereby a D- or L-ketose is epimerized at position 3 to produce a corresponding D- or L-ketose; and
   (B) the highest substrate specificity for D-fructose and D-psicose among D- and L-ketoses,
   wherein the DNA comprises (a) or (b) below:
   (a) the base sequence of SEQ ID NO: 2 or SEQ ID NO: 3, or
   (b) a DNA encoding the amino acid sequence of SEQ ID NO: 1.

2. The recombinant expression vector according to claim 1, wherein the ketose 3-epimerase has the following physical and chemical properties (a) to (f):
   (a) molecular weight,
      a homotetramer structure having a subunit molecular weight of 32 kDa, with a subunit molecular weight of about 32 kDa as measured by SDS-PAGE, and a molecular weight of 120 kDa as measured by gel filtration;
   (b) optimal pH,
      6 to 11 under 30° C., 30-min reaction conditions in the presence of 20 mM magnesium ($Mg^{2+}$);
   (c) optimal temperature,
      60 to 80° C. under pH 7.5, 30-min reaction conditions in the presence of 20 mM magnesium ($Mg^{2+}$);
   (d) pH stability,
      stable in at least a pH range of 5 to 11 under 4° C., 24-hour maintained conditions;
   (e) heat stability,
      stable at about 50° C. or less under pH 7.5, 1-hour maintained conditions in the presence of 4 mM magnesium ions ($Mg^{2+}$), and stable at about 40° C. or less in the absence of magnesium ions ($Mg^{2+}$); and
   (f) metal ion activation,
      activatable by divalent manganese ions ($Mn^{2+}$), divalent cobalt ions ($Co^{2+}$), and calcium ($Ca^{2+}$) and magnesium ions ($Mg^{2+}$).

3. The recombinant expression vector according to claim 1, wherein the ketose 3-epimerase has the following substrate specificities 1 to 8:
   1. 43.8% relative activity for a D-fructose substrate;
   2. 100% activity for a D-psicose substrate;
   3. 1.13% relative activity for a D-sorbose substrate;
   4. 18.3% relative activity for a D-tagatose substrate;
   5. 0.97% relative activity for an L-fructose substrate;
   6. 21.2% relative activity for an L-psicose substrate;
   7. 16.6% relative activity for an L-sorbose substrate; and
   8. 44.0% relative activity for an L-tagatose substrate, the relative activity for each ketose being an activity relative to the epimerization activity for D-psicose which is taken as 100.

4. A transformant comprising the recombinant expression vector according to claim 1.

5. A transformant comprising the recombinant expression vector according to claim 2.

6. A transformant comprising the recombinant expression vector according to claim 3.

7. A method of producing ketose 3-epimerase, comprising a step of culturing the transformant according to claim 4, wherein the transformant produces the ketose 3-epimerase in a culture thereof.

8. The method according to claim 7, wherein the ketose 3-epimerase is collected from the culture of the transformant.

* * * * *